United States Patent [19]

Nakamura et al.

[11] Patent Number: 4,736,748

[45] Date of Patent: Apr. 12, 1988

[54] BLOOD COMPONENT MONITORING SYSTEM

[75] Inventors: Michihiro Nakamura, Soja; Makoto Yano, Kurashiki, both of Japan

[73] Assignee: Kuraray Co., Ltd., Okayama, Japan

[21] Appl. No.: 34,026

[22] Filed: Apr. 3, 1987

[30] Foreign Application Priority Data

Apr. 5, 1986 [JP] Japan .................................. 61-78881

[51] Int. Cl.$^4$ ............................................... A61B 5/00
[52] U.S. Cl. ......................................... 128/632; 604/4
[58] Field of Search .......................... 128/63 V; 604/4; 422/68

[56] References Cited

U.S. PATENT DOCUMENTS

| | | | |
|---|---|---|---|
| 4,119,406 | 10/1978 | Clemens | 128/632 X |
| 4,334,541 | 6/1982 | Leist et al. | 128/632 |
| 4,516,580 | 5/1985 | Polanyi | 128/632 |
| 4,585,007 | 4/1986 | Uchigaki et al. | 128/632 |

OTHER PUBLICATIONS

Automated PO$_2$, PCO$_2$ and pH Monitoring of Infants by Clark et al, Computers and Biomedical Research 4,262,274 (1971).

Online Patient-Monitoring System for the Simultaneous Analysis to Blood K+, Ca2+, Na+ and pH Using a Quadruple-Function ChemFET Integrated Circuit Sensor, A. Sibbald et al., Med. & Biol. Eng. & Comput., 1985, 23,329–338.

Primary Examiner—Edward M. Coven
Attorney, Agent, or Firm—Birch, Stewart, Kolasch & Birch

[57] ABSTRACT

A blood component monitoring system for monitoring chemical substances of interest in blood, which includes a transfusion circuit including a flow-through cell adapted to be fluid-connected with a blood vessel through an indwelling catheter, a reservoir for accommodating a quantity of physiologically compatible sensor correcting solution, a connecting tubing extending between the reservoir and the flow-through cell and a transfusion pump; a detector unit including a temperature sensor and a chemical sensitive sensor device both incorporated inside the flow-through cell. A transfusion pump drive circuit is provided for controlling operation of the transfusion pump, a sensor drive circuit is provided for driving the temperature sensor and the chemical sensitive sensor device, a processing unit is provided for controlling both of the transfusion pump drive circuit and the sensor drive circuit and for reading respective outputs from the temperature sensor and the chemical sensitive sensor device and converting the outputs into respective measured values, and an output device is provided for externally outputting the measured values.

10 Claims, 14 Drawing Sheets

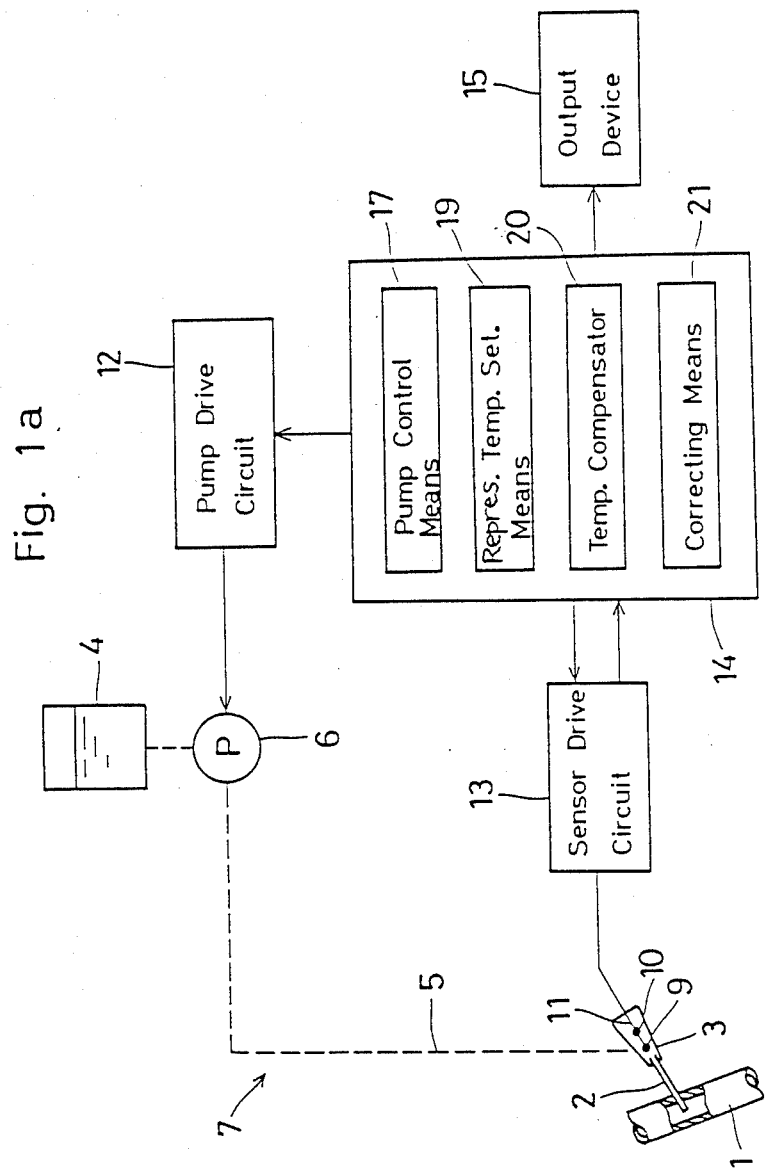

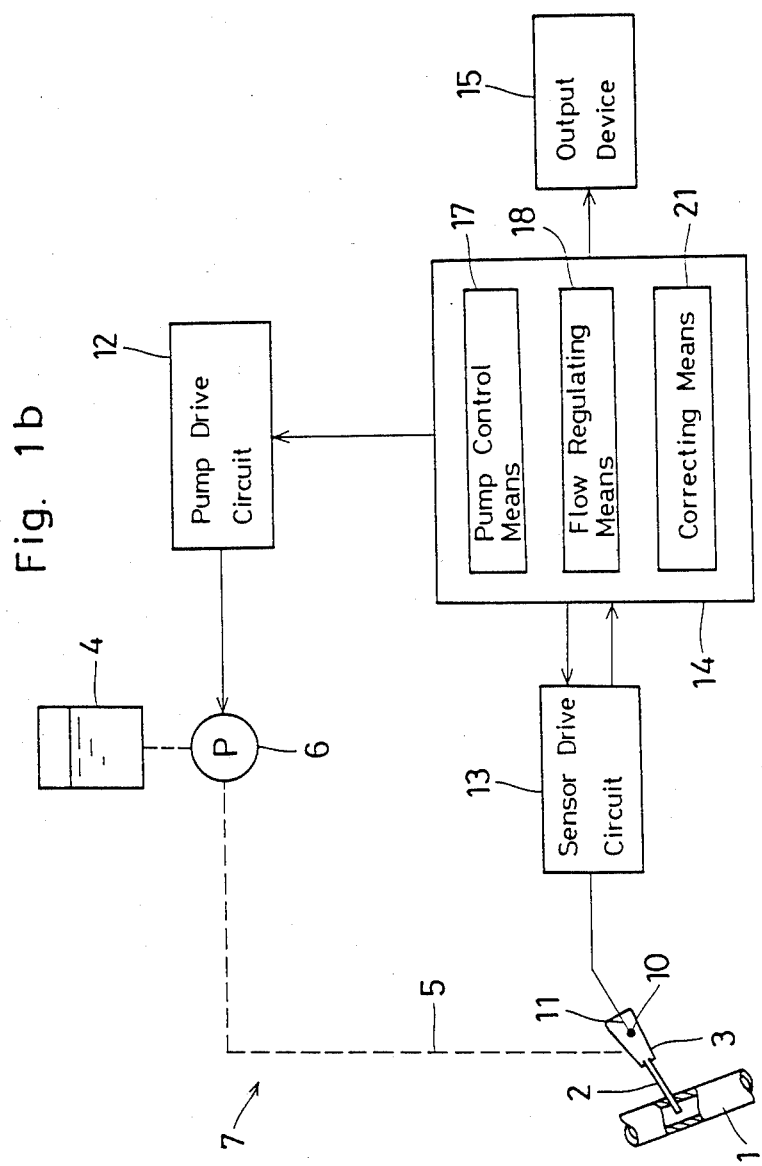

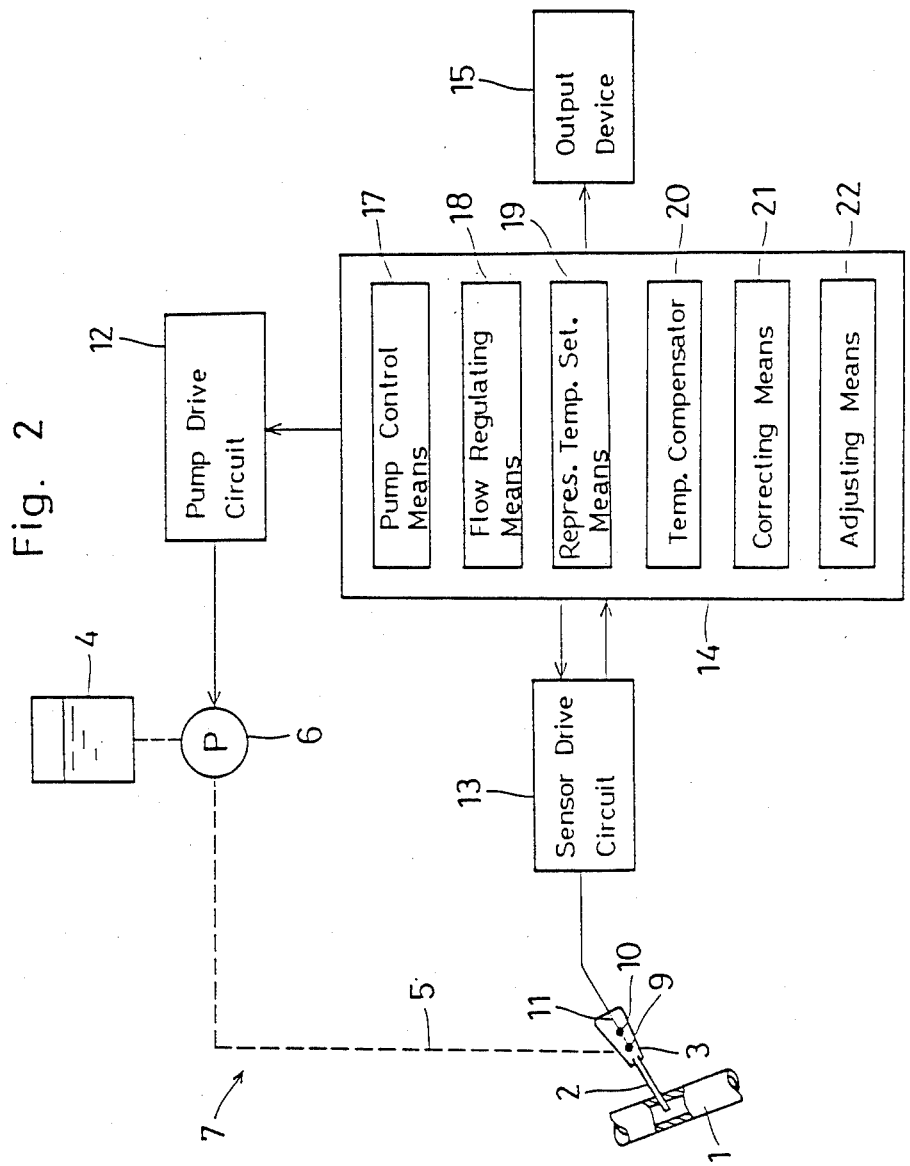

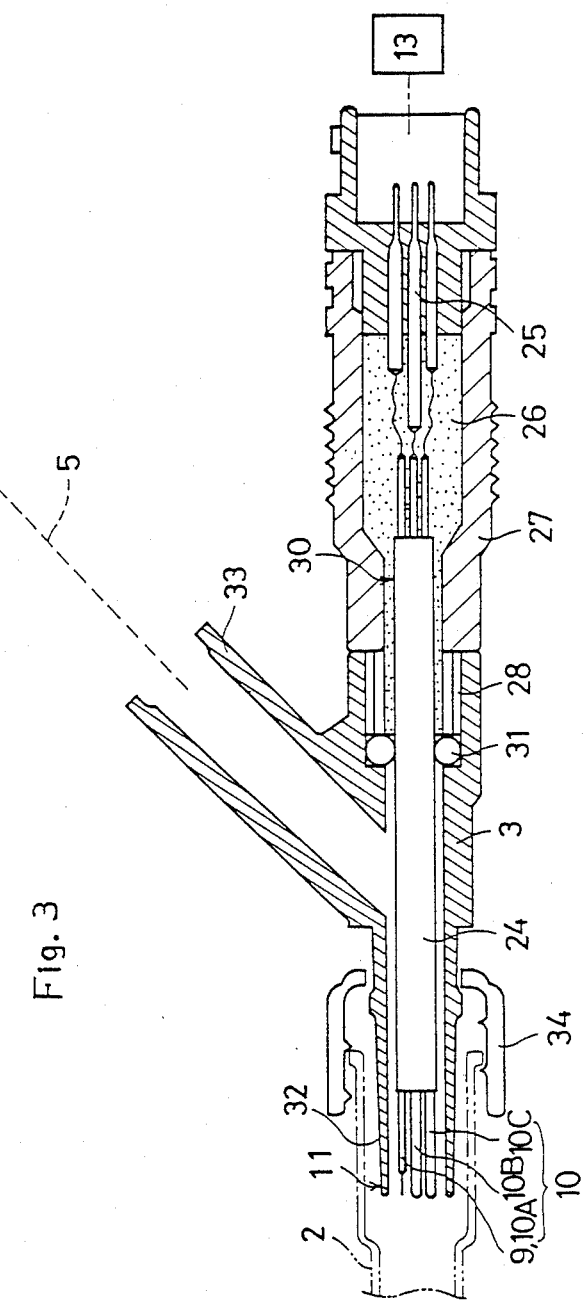

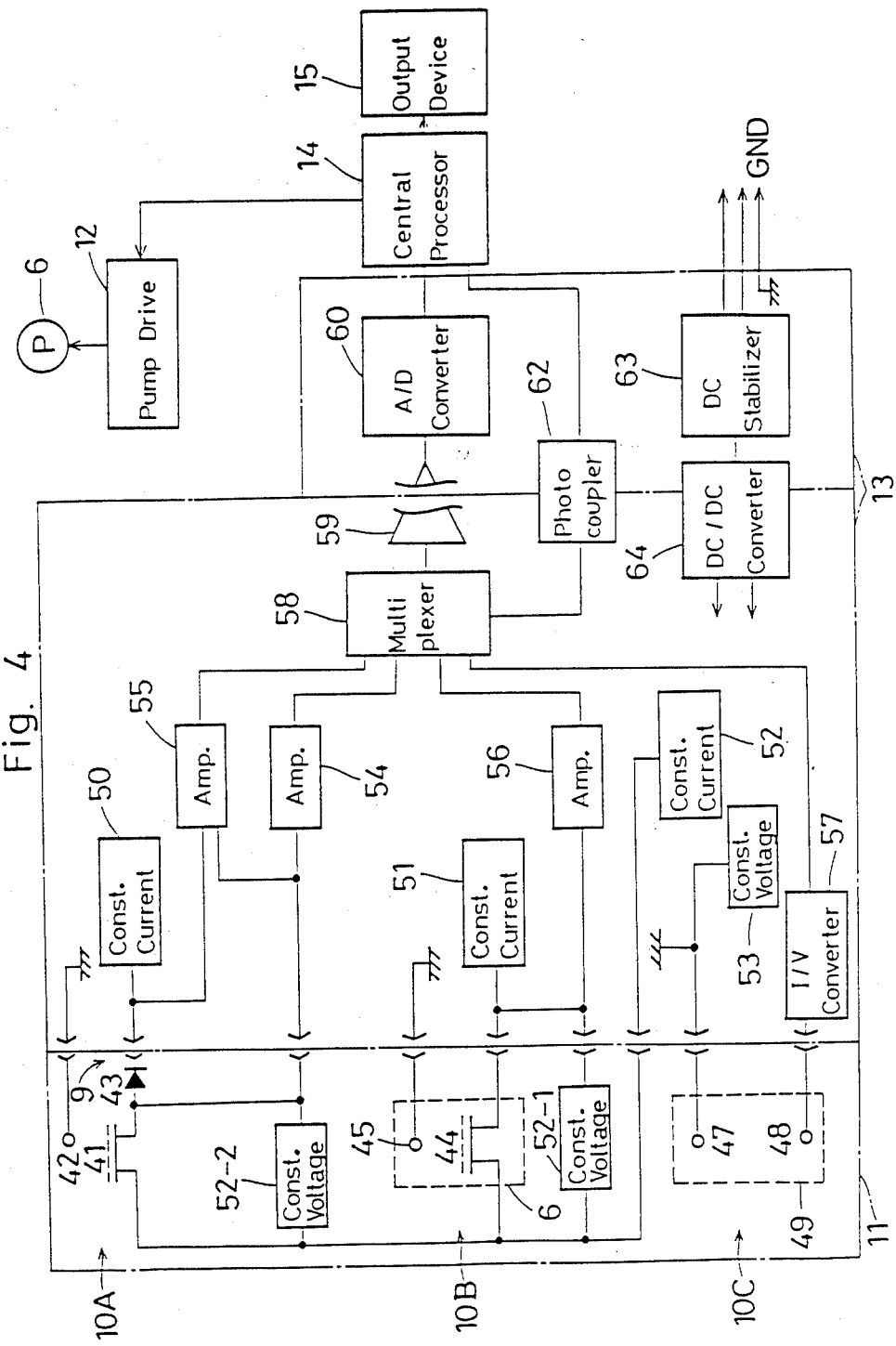

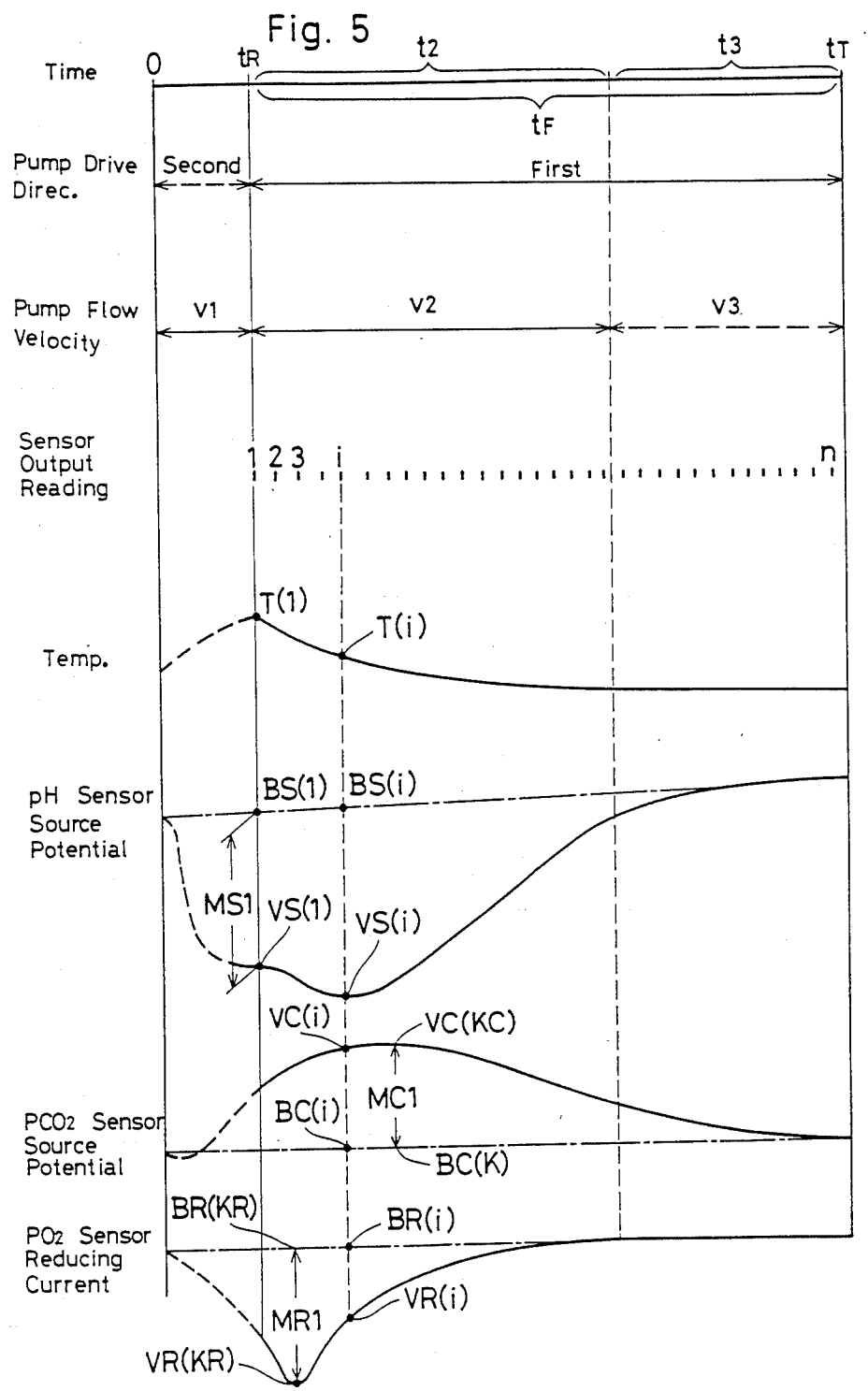

BLOOD COMPONENT MONITORING SYSTEM

BACKGROUND OF THE INVENTION

1. Field of the Invention

The present invention generally relates to a blood component monitoring system for measuring and/or intermittently monitoring the concentration or partial pressure of chemical components contained in blood and, more particularly, to a system for measuring and/or monitoring the concentration or partial pressure of chemical components of interest contained in blood by the use of a flow-through cell, into which blood is intermittently extracted through an indwelling catheter or cannula inserted into the blood vessel, and temperature and chemical component sensors both diposed within the flow-through cell, with no need to drain the extracted blood outside the system.

2. Description of the Prior Art

The continuous or intermittent measurement of chemical properties of one or more precious substances contained in blood such as represented by, for examaple, gaseous components such as oxygen and carbon dioxide, ions such as hydrogen, sodium, potassium, calcium and chlorine, or compositions such as glucose, urea, uric acid and creatinine, is nowadays one of the important therapeutic procedures necessary to monitor the pathological status of a patient, to administer the anesthesia during a surgical operation and/or to monitor the therapeutic effect. The method for the continuous measurement of the chemical properties of blood components broadly includes that for in vivo application wherein a chemcial component sensor device is implanted or introduced percutaneously and that for ex vivo application wherein the chemical component sensor device is disposed in an extracorporeal circuit and blood is introduced to the sensor device.

The in vivo system is effective to measure the concentration of a chemcial component of interest at a particular site of the blood vessel. However, since the chemical component sensor device is required to be indwelled or implanted in the blood vessel, and, on the other hand, since the size of the available chemical component sensor device is limited, it is difficult to manufacture the chemical component sensor device that is selectively sensitive to a plurality of substances contained in the blood. Moreover, while it is well known that the indwelling component sensor device is constantly in contact with the blood within the blood vessel and is susceptible to a drift in output characteristics as a result of adsorption of protein, correction cannot be effected without difficulty once the component sensor device has been indwelled in the blood vessel. In view of these problems, the in vivo system has not yet found wide applications in a clinical situations.

In contrast thereto, the ex vivo system is expected to find an increasing application. In particular since the component sensor device is used ex vivo and, therefore, the size of the component sensor device does not matter, the component sensor device which is selectively sensitive to a plurality of substances can easily be made. Further, since an automatic drift correction can easily be embodied and the component sensor device can be regularly cleansed, a stabilized measurement for a prolonged time is possible.

The ex vivo blood component monitoring apparatus, that is, the blood component monitoring apparatus using the sensor device for ex vivo application, is currently available in two types; a blood drain type and a blood recirculating type. In the blood drain type, blood extracted from the blood vessel for the measurement is drained out of the system after the measurement has been done and has merit in that neither the component sensor device nor a correcting fluid need be sterilized, but is deficient in that the valuable blood used for the measurement is discarded. On the other hand, in the blood recirculating type, the blood extracted from the blood vessel for the measurement is circulated back to the blood vessel after the measurement has been made and has merit in that the valuable blood is returned to the patient without being drained out of the system, although there are requirements that the component sensor device must be sterilized and the correcting fluid should, because it is infused into the blood vessel together with the recirculated blood, be sterile and harmless to the patient.

The ex vivo blood component monitoring apparatus of blood drain type includes, for example, a pH, $PCO_2$, and $PO_2$ monitor disclosed by J. S. Clark et al. in 1971 (See Computers and Biomedical Research 4, 262 [1971]) and a monitor for the analysis of blood potassium, sodium, calcium and hydrogen ions disclosed by A. Sibbald et al. in 1985 (See Medical and Biological Engineering & Computing 23, 329 [1985]). In these prior art monitoring apparatuses, a multi-chemical sensitive sensor device used therein is disposed in a constant temperature bath fluid-connected with the indwelling catheter through a tubing for the introduction of blood from the indwelling catheter to the constant temperature bath during the measurement, the blood being discarded out of the system after the actual measurement. A major disadvantage inherent in the ex vivo monitoring apparatus of the blood drain type lies in that the blood is discarded. Except for the cases receiving a surgical operation while being blood-transfused, it can hardly be regarded tolerable to drain a few tens milliliters of blood per day out of the system from a severely ill patient only for the purpose of measurement of chemical properties of substances contained in the blood.

An example of the ex vivo monitoring apparatus of blood recirculating type includes a blood component monitoring apparatus of the transfusion type disclosed in, for example, the Japanese Laid-open Patent Publication No. 55-76639 published June 9, 1980, the invention of which has been assigned to the same assignee of the present invention. According to this publication, the chemical sensitive sensor device is mounted in an indwelling catheter indwelled in the blood vessel and fluid-connected with a transfusion tubing through which a physiologically compatible liquid being transfused for the correction of the sensor device is supplied, and blood is extracted into the sensor device at any desired time during the transfusion taking place for the measurement of the chemical properties of substances contained in the blood. The blood so extracted into the sensor device is, after the measurement, circulated back to the blood vessel together with the physiologically compatible liquid being transfused. The monitoring apparatus of transfusion type referred to above has subsequently been improved, the improved versions of which are disclosed in the Japanese Laid-open Patent Publications No. 59-155240 and No. 60-116332 published Sept. 4, 1984, and June 22, 1985, respectively.

During the course of a series of experiments conducted on animals with the use of the above described monitoring apparatus of the transfusion type with a view to commercializing the apparatus, the inventors of the present invention have encountered with the following problems.

(1) Even in the system, such as in the above described monitoring apparatus of the transfusion type, wherein the measurement is carried out while blood is intermittently extracted, adsorption of protein, blood cells, fibrinogen and some other substances contained in the blood to the chemical sensitive sensor device occurs with the consequence that the response of the chemical sensitive sensor device tends to be lowered, even though the degree of adsorption is small as compared with that exhibited by the chemical sensitive sensor device for in vivo application wherein constant contact between the chemical sensitive sensor device and the blood takes place.

(2) Since the temperature of the site at which detection is made tends to change during a single pumping cycle during which the blood is extracted and then circulated back to the blood vessel, the temperature dependent change of the chemical sensitive sensor device must be compensated for.

(3) While the particular parameters of the chemical sensitive sensor device are determined with the use of a control solution prepared to provide a replica of blood plasma, it has been found that, even though the concentration of chemical components remains substantially the same between the control solution and the actual blood, the chemical sensitive sensor device tends to give different output characteristics between the control solution and the actual blood during the same pumping cycle, and therefore, this leads to an error occurring during the actual measurement of the chemical properties of the substances contained in the blood.

The problem (1) discussed above may be obviated substantially if the chemical sensitive sensor device used is frequently replaced with fresh sensor devices of identical construction to avoid the adverse influence brought about by the absorption of the chemical substances, and the problem (3) discussed above may not be crucial in the case of the chemical sensitive sensor device for use in the measurement of $PCO_2$ which exhibits a relatively small change in output characteristic between the control solution and the actual blood.

SUMMARY OF THE INVENTION

The present invention has been devised with a view to substantially eliminating the above discussed problems, particularly the problem (2) discussed above, and has for its essential object to provide an improved chemical component monitoring apparatus wherein the temperature dependent change of the chemical sensitive sensor device is properly compensated for to achieve an accurate measurement of chemical properties of substances contained in blood.

The present invention has also been devised with a view to substantially eliminating the problem (1) discussed above, and has for its important object to provide an improved blood component monitoring apparatus wherein the chemical sensitive sensor device is rinsed with a physiologically compatible liquid to avoid the substantial lowering of the response of the chemical sensitive sensor device.

Broadly speaking, the blood component monitoring apparatus required to accomplish the first mentioned object of the present invention is constructed as shown in FIG. 1(a) of the accompanying drawings, reference to which will now be made. As shown therein, a transfusion circuit, generally identified by 7, includes a flow-through cell 3 connectable directly with an indwelling catheter 2 punctured into a blood vessel 1, a transfusion reservoir 4, a tubing 5 extending between the flow-through cell 3 and the transfusion reservoir 4, and a transfusion pump 6 disposed on the tubing 5 intermediately between the flow-through cell 3 and the transfusion reservoir 4. A detector 11 includes a temperature sensor 9 and a chemical sensitive sensor device 10 sensitive to one or more chemical substances contained in blood, both the temperature sensor 9 and the chemical sensitive sensor device 10 being disposed within a flow-through cell 3.

In addition to the transfusion circuit 7 and the detector 11, the apparatus also includes a transfusion pump drive circuit 12 for controlling the transfusion pump 6, a sensor drive circuit 13 for driving the temperature sensor 9 and the chemical sensitive sensor device 10, a processing device 14 for controlling the transfusion pump drive circuit 12 and the sensor drive circuit 13 simultaneously and for reading an output from the chemical sensitive sensor device 10 and converting the output into a measured value, and an output device 15 including for example, a display unit, for providing a visual indication of the measured value.

The processing device 14 includes a pump control device 17, a representative temperature setting device 19, a temperature compensating device 20, and correcting device 21. The processing device 14 is programmed to cause the pump control device 17 to control the transfusion pump drive circuit 12 so that the transfusion pump 6 can be driven according to a predetermined operating program alternately in a first direction required to transfuse a physiologically compatible solution from the flow-through cell 3 towards the blood vessel 1 and a second, opposite direction required to extract blood from the blood vessel 1 towards the flow-through cell 3. The representative temperature setting means 19 temperature representative of the temperature of the detector 11 detected by the temperature sensor 9 at a particular time during each pumping cycle with the transfusion pump 6 driven according to the predetermined operating program. The temperature compensating device 20 converts the output from the chemical sensitive sensor device 10 into an output representative of the representative temperature according to a predetermined temperature compensating equation on the basis of the output from the chemical sensitive sensor device 10 and the output from the temperature sensor 9 both read during each pumping cycle while the transfusion pump 6 is being driven according to the predetermined operating program. The correcting device 21 corrects a characteristic value, based on the amplitude of the converted output, according to a predetermined correction equation, to calculate the concentration of one or more chemical substances in the blood and then to apply a signal indicative of the calculated concentration to the output device 15.

Again broadly speaking, the blood component monitoring apparatus required to accomplish the second mentioned object of the present invention makes use of, as shown in FIG. 1(b) of the accompanying drawings, a flow regulator 18 while such elements as associated with the compensation for the temperature dependent change are not utilized. More specifically, as shown in FIG. 1(b), the blood component monitoring apparatus required to accomplish the second mentioned object of the present invention includes a transfusion circuit 7 having a flow-through cell 3, a transfusion pump 6 and a tubing 5 connecting the flow-through cell 3 and the transfusion pump 6, a detector 11 having a chemical sensitive sensor device 10 sensitive to one or more chemical substances contained in the blood, a transfusion pump drive circuit 12, a sensor drive circuit 13 and a processing device 14 with a pump control device 17, a flow regulating device 18 and a correcting device 21. The flow regulating means 18 is operable to control the flow to establish the following relationship.

$$4.0 \leq QF/QR \leq 30$$

wherein QF represents the positive flow volume or the volume of flow of a physiologically compatible solution during the drive of the transfusion pump 6 in a first direction, and QR represents the reverse flow volume or the volume of flow of physiologically compatible solution during the drive of the transfusion pump 6 is a second direction opposite to the first direction.

According to the present invention, since the transfusion pump 6 is alternately driven by the pump control means 17 in one of the first and second directions opposite to each other according to the predetermined operating program, the physiologically compatible solution and the blood are alternately introduced into the flow-through cell 3 so that the chemical sensitive sensor device 10 can correspondingly alternately detect chemial properties of the physiologically compatible solution and the blood. Therefore, it is possible to measure the chemical properties of substances contained in the blood while operating characteristics of the chemical sensitive sensor device 10 is corrected by the physiologically compatible solution.

Moreover, not only does the temperature inside the flow-through cell 3 in which the chemical sensitive sensor device 10 is disposed change with the ambient temperature, but it also undergoes a change even during each pumping cycle because, during each pumping cycle, the physiologically compatible solution and the blood of different temperatures flow in and out of the flow cell 3 at a varying mixing ratio. Accordingly, the output signal from the chemical sensitive sensor device 10 itself cannot be used as a data utilizable directly for the measurement of the chemical properties of the blood susbstances.

In view of the foregoing, according to one aspect of the present invention, the representative temperature setting device 19 is utilized to determine the representative temperature during each pumping cycle and, on the other hand, the temperature compensating device 20 is utilized to effect a temperature compensation according to the predetermined temperature compensating equation to the output from the chemical sensitive sensor device 10 in reference to both of the outputs read from the temperature sensor 9 and the chemical sensitive sensor device 10 during each pumping cycle. The correcting device 21 is also utilized to correct the temperature compensated output according to the predetermined correction equation to give the concentration of the blood substances. In this way, the accurate measurement of the concentration of the blood substances, the temperature dependent change of which has been eliminated, can be accomplished.

According to another aspect of the present invention, in the blood component monitoring apparatus so designed as to accomplish the second mentioned object, since the positive flow volume, that is, the volume of flow of the physiologically compatible solution from the flow-through cell 3 into the blood vessel 1, is sufficiently greater than the reverse flow volume, that is, the volume of flow of the blood from the blood vessel 1 to the flow-through cell 3, the chemical sensitive sensor device 10 contaminated with substances contained in the blood can be sufficiently rinsed by the physiologically compatible solution.

It is to be noted that, in the blood component monitoring apparatus specifically designed to accomplish the second mentioned object, the flow-through cell is, during the use of the apparatus, accommodated within a constant temperature bath to keep the temperature of the flow-through cell at a predetermined temperature so that a relatively highly precise measurement can be accomplished with no need to effect the compensation for temperature dependent change. However, the use of the constant temperature bath may be obviated if the measurement suffices to be relatively less precise, and where the temperature dependent change is required to be compensated for in order to accomplish a relatively highly precise measurement without using the constant temperature bath. The blood component monitoring apparatus specifically designed to accomplish the second mentioned object can be designed to accomplish both of the first and second mentioned objects by the employment of a temperature compensating technique or a technique of extracting blood at appropriate time intervals, then measuring chemical properties of substances contained in the blood by the use of a blood component measuring device and finally outputting the measured value, both similar to that used in the blood component monitoring apparatus specifically designed to accomplish the first mentioned object.

BRIEF DESCRIPTION OF THE DRAWINGS

The present invention will become more clearly understood from the following description of preferred embodiments, when taken in conjunction with the accompanying drawings. However, the embodiments and the drawings are given only for the purpose of illustration and explanation, and are not to be taken as being limitative of the present invention in any way whatsoever, whose scope is to be determined solely by the appended claims. In the drawings, like reference numerals denote like parts in the several views, and:

FIGS. 1(a) and 1(b) are schematic block diagrams showing a blood component monitoring apparatus according to the present invention, which illustrate respective principles necessary to accomplish the different objects of the present invention;

FIG. 2 is a schematic block diagram showing the blood component monitoring apparatus according to a first preferred embodiment of the present invention;

FIG. 3 is a longitudinal sectional view, on an enlarged scale, showing the details of a flow-through cell used in the blood component monitoring apparatus;

FIG. 4 is a circuit block diagram showing the details of an electric circuit of the blood component monitoring apparatus;

FIG. 5 is a timing chart showing an operating program for a transfusion pump and response curves of respective sensors after the correction of the temperature dependent change;

DETAILED DESCRIPTION OF THE EMBODIMENTS

Figure 6:
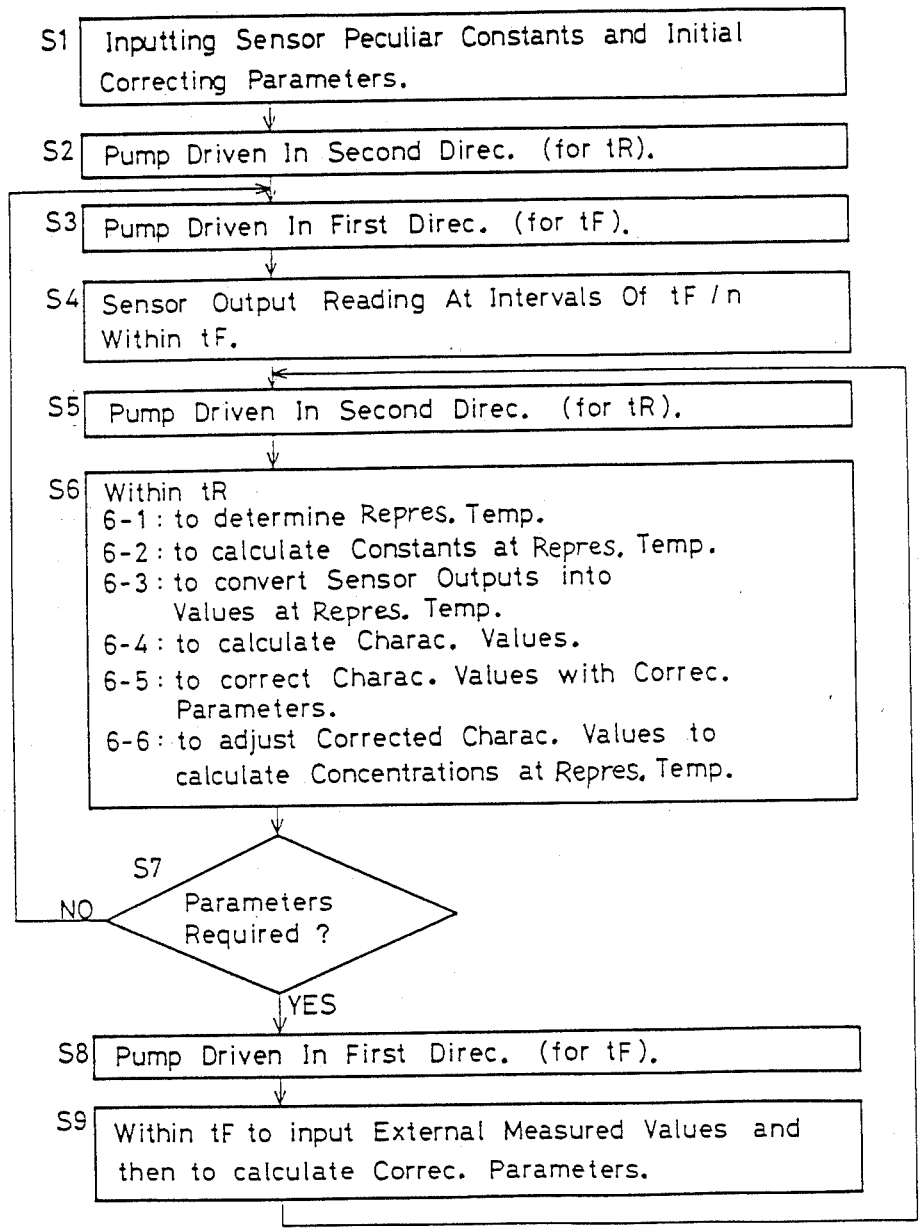
FIG. 6 is a flow chart showing the sequence of operation of a processing device used in the blood component monitoring apparatus.

In describing the details of the blood component monitoring apparatus according to the present invention with reference to FIG. 2, what has been described in connection with the principles thereof shown in and with reference to FIGS. 1(a) and 1(b) will not be reiterated for the purpose of brevity. As shown in FIG. 2, the processing device 14 is shown to include an adjusting device 22 in addition to the pump control device 17, the flow regulating device 18, the representative temperature setting device 19, temperature compensating device 20 and the correcting device 21.

The blood component monitoring apparatus according to this first preferred embodiment of the present invention has the following functions.

(A) Causing the pump control device 17 to drive the transfusion pump 6 according to a predetermined flow-time program alternately in a first direction required to transfuse a physiologically compatible solution from the flow-through cell 3 towards the blood vessel 1 and a second, opposite direction required to extract blood from the blood vessel 1 towards the flow-through cell 3;

(B) Causing the flow regulating device 18 to control the flow to establish the following relationship, $$4.0 \leq QF/QR \leq 30$$

wherein QF represents the positive flow volume or the volume of flow of a physiologically compatible solution during the drive of the transfusion pump 6 in a first direction, and QR represents the reverse flow volume or the volume of flow of the physiologically compatible solution during the drive of the transfusion pump 6 in a second direction opposite to the first direction;

(C) Causing the representative temperature setting device 19 to adopt as a representative temperature the temperature of the detector 11 detected by the temperature sensor 9 at a particular time during each pumping cycle with the transfusion pump 6 driven according to the predetermined flow-time program;

(D) Causing the temperature compensating device 20 to convert the output from the chemical sensitive sensor device 10 into an output corresponding to the representative temperature, determined by the function (A) above, according to a predetermined temperature compensating equation on the basis of the output from the chemical sensitive sensor device 10 and the output from the temperature sensor 9 both read out simultaneously during each pumping cycle while the transfusion pump 6 is being driven according to the predetermined flow-time program, and correcting the amplitude, or a value equivalent of such amplitude, of the converted output curve during each pumping cycle, that is, the characteristic value based on the amplitude, according to a predetermined correction equation to calculate the concentration of one or more chemical substances in the blood; and (E) Causing the adjusting device 22 to adjust the concentration of the chemical substances calculated by the function (D) above so that the measurement of the concentration of substances in the blood which is given by the blood component monitoring apparatus according to the present invention can match with the measurement of the concentration of the same substances in the same blood which is given by a separate apparatus different from the blood component monitoring apparatus of the present invention.

Of these functions (A) to (E), the function (A) is a basic function inherent in the blood component monitoring apparatus of the transfusion type. The remaining functions (B) to (E) referred to above are introduced as means for substantially solving the problems (1) to (3) discussed hereinbefore. More specifically, function (B) constitutes means for substantially avoiding any possible reduction in response of the chemical sensitive sensor resulting from the adsorption of blood substances to the chemical sensitive sensor as discussed under item (1) hereinbefore; a functions (C) and (D) constitute a means for effecting the compensation for the temperature dependent change as discussed under item (2) hereinbefore; and the function (E) constitutes means for substantially eliminating any possible difference in output of the chemical sensitive sensor between the control solution and the blood as discussed under item (3) hereinbefore.

Hereinafter, each of these functions (A) to (E) will be described in connection with the blood component monitoring apparatus of the transfusion type designed to measure the pH value and the concentration of any one of $PCO_2$ and $PO_2$ contained in blood.

FIG. 3 illustrates, in a longitudinal sectional view, the details of the flow-through cell 3 accommodating therein the chemical sensitive sensor device 10. As shown therein, the chemical sensitive sensor device 10 is a multi-chemical sensitive sensor including a pH sensor 10A having an ion sensitive field effect transistor (ISFET), a $PCO_2$ sensor 10B also with an ion sensitive field effect transistor (ISFET) and a Clark's $PO_2$ sensor 10C. The pH sensor 10A has the temperature sensor 9 built-in so that the temperature inside the detector 11 can be measured.

The flow-through cell 3 includes a generally elongated block 24 of synthetic resin molding having one end carrying the sensors 10A to 10C and having connecting wirings embedded therein for connecting the sensors 10A to 10C with respective input/output pins, generally identified by 25, which pins 25 are rigidly carried by a tubular connector 27 which is threaded at 28 to the flow-through cell 3 in a coaxial relationship. The opposite end of the elongated block 24 received in the tubular connector 27, together with electric wirings extending outwardly from such opposite end of the elongated block 24 an the associated input/output pins 25, held immobile within the connector 27 filled with an electrically insulating material 26. The connector 27 carrying the elongated block 27 with the sensors 10A to 10C protruding outwardly from that end of the elongated block 27 constitutes a multi-chemical sensitive sensor assembly 30 that can be removably coupled with the flow-through cell 3. An O-ring seal 31 generally interposed between the sensor assembly 30 and the flow-through cell 3 provides a fluid-tight seal therebetween when the sensor assembly 30 is threaded to the flow-through cell 3.

The flow-through cell 3 is in the form of a generally Y-shaped tubular member having an outwardly tapering section 32 for insertion into an indwelling catheter 2 and a coupling section 33 for fluid-connection with the tubing 5, said outwardly tapering section 32 having a lure lock 34 mounted thereon for ensuring a firm connection between the flow-through cell 3 and the indwelling catheter 2 once both are coupled together.

An electric circuit arrangement of the blood component monitoring apparatus of transfusion type for the measurement of the pH value and the concentration of $PCO_2$ and $PO_2$ is shown in FIG. 4 in the form of a block diagram. Referring to FIG. 4, reference numeral 41 represents the ion sensitive field effect transistor (pH-ISFET) forming a part of the pH sensor 10A, reference numeral 42 represents a reference electrode for the pH sensor 10A, and reference numeral 43 represents a temperature sensing diode integrated together with the pH-ISFET 41. Reference numeral 44 represents a pH-ISFET forming a part of the $PCO_2$ sensor, reference numeral 45 represents a reference electrode for the $PCO_2$ sensing pH-ISFET 44, and reference numeral 46 represents a gas permeable membrane for the $PCO_2$ sensor. Reference numeral 47 represents an anode for the $PO_2$ sensor, reference numeral 48 represents a cathode for the $PO_2$ sensor, and reference numeral 49 represents a gas permeable membrane for the $PO_2$ sensor.

The electric circuitry shown in FIG. 4 includes constant current circuits 50 and 51 for supplying a predetermined drain current to the field effect transistors 41 and 44 for the pH sensor and the $PCO_2$ sensor, respectively; constant voltage sources with direct current 52-1 and 52-2 for supplying drain voltage to the field effect transistors 41 and 44, respectively; a constant current circuit 52 operable to avoid any possible flow of an excessive current, higher than a predetermined value, to both of the field effect transistors 41 and 44 in the event that any one of the field effect transistors 41 and 44 is short-circuited by reason of an accident; a voltage source with direct current 53 for supplying a predetermined voltage between the anode and the cathode of the $PO_2$ sensor; amplifiers 54 and 55 for reading the source potential and the diode potential of the field effect transistor 41 for the pH sensor; an amplifier 56 for reading the source potential of the field effect transistor 44 for the $PCO_2$ sensor; and a current-to-voltage converter 57 for reading a reducing current of the $PO_2$ sensor.

The electric circuitry also includes a multiplexer 58 for selecting respective outputs fed from the amplifiers 54, 55 and 56 and the current-to-voltage converter 57 and supplying it to an isolation amplifier 59; an analog-to-digital converter 60; a central processor 14 having, for example, a microcomputer, a direct current stabilizing power source 63, a DC/DC converter 64 utilizing a magnetic coupling, the pump drive circuit 12 operated by a signal from the central processor 12 operated by a signal from the central processor 14 for controlling the operation of the transfusion pump 6, and the output device 15 with a display unit capable of providing a visual indication of results of measurement such as measured figures and graphs. The multiplexer 58 is operated by a signal fed from the central processor 14 through the photo-coupler 62. The isolation amplifier 59, the photo-coupler 62 and the DC/DC converter 64 are utilized to electrically isolate the detector 11, coupled with a living body, from the sensor drive circuit 13, the power source 63 and the central processor 14.

As described above, the blood component monitoring apparatus of the transfusion type incorporating the above described electric circuitry is systematized with the transfusion circuit 7 including the transfusion pump 6, the reservoir 4, the tubing 5 and the flow-through cell 3, the detector 11, the pump control circuit 12, the sensor drive circuit 13, the central processor 14 and the output device 13. Since the blood component monitoring apparatus is for medical use, the sensor drive circuit 13 is isolated as hereinbefore described so that any possible leakage of current from the detector 11 to the living body being examined can be minimized.

The apparatus as hereinbefore described is operated under the following operating conditions. Before the description thereof proceeds, operating conditions for the field effect transistors 41 and 44 for the pH and $PCO_2$ sensors, respectively, will be described. The ion sensitive field effect transistors 41 and 44 were used having their channel characteristic values $\beta$ within the range of 200 to 300 $\mu A/V^2$. The drain voltage used is within the range of 3 to 5 volts, and the drain current was selected to be within the relatively low range of 5 to 10 $\mu A$. This is because, as discussed in the Japanese Laid-open Patent Publications No. 60-4851 and No. 60-225056, published Jan. 11 and Nov. 9, 1985, respectively, the temperature dependent characteristic of the source potential of the pH sensitive field effect transistor at a relatively low drain current exhibits a linear characteristic and the compensation of the temperature dependent change can, therefore, be readily accomplished. The source potentials of the pH sensitive field effect transistors 41 and 44 of the pH sensor 10A and the $PCO_2$ sensor 10B relative to the reference electrodes 42 and 45 are within the range of $-0.5$ to $+2.0$ volts.

The $PO_2$ sensor 10C has its anode grounded and its cathode 48 connected with a galvanometer 57. The direct current voltage applied between the anode and the cathode was 0.6 volt. The reducing current of the $PO_2$ sensor 10C was normally within the range of 0 to 500 nA.

In the blood component monitoring apparatus according to the present invention, the physiologically compatible solution serves as a control solution for the correction of any one of the sensors and should be harmless to the patient when transfused for a prolonged period of time. The following physiologically compatible solutions have been found appropriate for use with sensors sensitive to the following substances.

Normal saline solution:
$PCO_2$, $PO_2$, $Na^+$ and $Cl^-$ sensors
Ringer's solution:
$PCO_2$, $PO_2$, $Na^+$, $K^+$, $Ca^{2+}$, $Cl^-$ sensors
Ringer's solution with lactic acid added:
$PCO_2$, $PO_2$, $Na^+$, $K^+$, $Ca^{2+}$, pH, $Cl^-$, Lactic acid ions sensors
Ringer's solution with glucose and lactic acid added:

K+, Ca2+, pH, Cl−, Lactic acid ions, Glucose sensors

Ringer's solution with sorbitol and lactic acid added: Na+, K+, Ca2+, pH, Cl−, Lactic acid ions sensors Any one of the Ringer's solution with lactic acid added, the Ringer's solution with glucose and lactic acid added and the Ringer's solution with sorbitol and lactic acid added may be used as the physiologically compatible solution for use in the blood component monitoring apparatus of the transfusion type for the measurement of the pH value and the concentration of $PCO_2$ and $PO_2$ now under discussion. The Ringer's solution added, however, with lactic acid, was mainly used during a series of experiments conducted with the use of the blood component monitoring apparatus according to the present invention.

The operating program of the apparatus during each pumping cycle is shown in FIG. 5. Assuming that the timing at which the transfusion pump 6 being driven in the first direction F is reversed so as to be driven in the second direction R opposite to the first direction F is at the point 0 in the graph of FIG. 5, the transfusion pump 6 is driven in the second direction R during a period between the timing 0 and the timing tR and in the first direction F during a period between the timing tR and the timing tT. Accordingly, assuming that $tF = tT - tR$, the time during which the pump 6 is driven in the first direction F and the time during which the pump 6 is driven in the second direction R are expressed by tF and tR, respectively, and the time required to complete each pumping cycle is expressed by tT. On the other hand, the fluid velocity of the flow of the physiologically compatible solution pumped by the transfusion pump 6 is set to be v1 during a period from the timing 0 to the timing tR, v2 during a period from the timing tR to the timing tR+t2, and v3 during a period from the timing tR+t2 to the timing tT.

While numerous time schedules according to which the outputs from the sensors are read out are possible, the time schedule employed in the apparatus now under discussion is such that the length of time from the timing tR to the timing tT was divided by n into a number of equal times, generally identified by i in the graph of FIG. 5, and the respective outputs from the four sensors 9, 10A, 10B and 10C shown in FIG. 4 were read out at intervals of a time tF/n starting from the timing tR. The period from the timing 0 to the timing tR in which the pump 6 is driven in the second direction was used for the calculation of the concentration and the partial pressure of the substances contained in the blood on the basis of the respective outputs from the sensors 9 and 10A to 10C so read out.

The graph of FIG. 5 also illustrates change in temperature during each pumping cycle and respective output curves VS(i), VC(i) and VR(i) of the pH, $PCO_2$ and $PO_2$ sensors after the temperature dependent changes have been compensated for, all of which will be discussed later.

Hereinafter, each of the functions (B) to (E) described as incorporated in the blood component monitoring apparatus according to the present invention for the purpose of substantially solving the problems inherent in the prior art apparatus of transfusion type will be discussed under separate headings in connection with the apparatus for the measurement of the pH value and the concentration of $PCO_2$ and $PO_2$.

Function (B)

This function is exhibited by the flow regulating device 18.

Countermeasures against the possible reduction in response of the sensor resulting from the adsorption of the blood substances on the sensing surface of the sensor will first be described. It has been found as a result of a series of experiments conducted with the use of animals that, even in the system, such as in the apparatus according to the present invention, wherein the sensor and the blood are intermittently brought into contact with each other, blood substances such as protein, blood cells and fibrinogen tend to adhere to the sensing surface of the sensor, causing the response of the sensor as a whole to be lowered. In particular, when the pH ion sensitive field effect transistor having its gate membrane formed of ceramics such as, for example, silicone nitride, is brought into direct contact with blood, it has been found that the response of the pH ion sensitive field effect transistor is lowered markedly. It has, however, been found that the addition of heparin, which is a blood anti-coagulant, to the Ringer' solution containing lactic acid which is used as the physiologically compatible solution in the practice of the apparatus of the present invention has been found effective to minimize the lowering of the response of the sensor.

When the apparatus according to the present invention was used, with no heparin added to the Ringer's solution containing lactic acid, in connection with the testing of dog's arterial blood, coagulation of blood substances on the sensor surface was clearly observed after several pumping cycles with the consequence that the response of each of the pH, $PCO_2$ and $PO_2$ sensors was reduced. However, when 1,000 to 20,000 units of heparin was added to one liter of the Ringer's solution containing lactic acid, the formation of blood clots was suppressed with the minimized reduction in response of each of the sensors, however, the reduction in response was observed after the measurement had been carried out for several hours. As a result of experiments conducted in an attempt to completely avoid the reduction in response of each of the sensors, it has been found that increase of the ratio of the positive flow QF of the transfusion pump relative to the reverse flow QR of the same transfusion pump for the purpose of prolonging the time during which the sensors are held in contact with the physiologically compatible solution and, on the other hand, shortening the time during which the sensors are held in contact with the blood is effective to achieve the minimized reduction in response of each of the sensors. Before the details thereof are described, the manner in which, and the condition under which, the operating program for the transfusion pump is formulated will be described.

Important factors for the operating condition of the transfusion pump from the clinical point of view are the net flow velocity q, in terms of milliliters per minute, of the physiologically compatible solution being transfused and the length of time tT, in terms of minutes, of each pumping cycle. The net flow velocity q is the volume of physiologically compatible solution transfused to the patient within a unit length of time and is, although variable depending on the weight of the patient and the metabolism of his or her liver and/or kidney, normally preferred to be not higher than 500 milliliters per 24 hours (or 0.347 milliliter per minute), preferably not higher than 200 milliliters per 24 hours (or 0.139 milliliter per minute) due to considerations of the metabolism of the kidney or other organs. On the other hand, the length of time of each pumping cycle should be selected to cope with the speed of change in composition of the blood and is normally not longer than 30 minutes, preferably not longer than 10 minutes.

The operating program in FIG. 5 illustrates, $$QR = v1 \cdot tR \quad (1)$$
$$QF = v2 \cdot t2 + v3 \cdot t3 \quad (2)$$
$$q = (QF - QR)/tT \quad (3)$$

wherein QR represents the positive flow volume induced by the transfusion pump, QR represents the reverse flow volume induced by the transfusion pump, and q represents the flow velocity of the physiologically compatible solution. If the ratio QF/QR is expressed by f, that is, $f=QF/QR$, the equation (3) can be rewritten as follows.

$$q \cdot tT = (f-1) \cdot QR \quad (4)$$

While the reverse flow volume QR is the volume required to flow the blood from the blood vessel 1 to the flow-through cell 3 through the indwelling catheter 2 as shown in FIG. 2, the reverse flow volume QR should be equal to at least the sum of the dead volumes of the indwelling catheter 2 and the flow-through cell 3.

Under these circumstances, the operating program for the pH, $PCO_2$ and $PO_2$ monitoring apparatus was formulated as follows.

| | |
|---|---|
| tR = | 0.67 minutes |
| tF = | 9.33 minutes |
| tT = | 10.00 minutes |
| t2 = | 4.33 minutes |
| t3 = | 5.00 minutes |
| v1 = | 0.42 milliliter per minute |
| n = | 56 |

Therefore, from the equation (1) above, the reverse flow volume reads 0.28 milliliter, that is, $QR = v1 \cdot tR = 0.28$ ml. This reverse flow volume so calculated is substantially equal to the sum (0.31 ml) of the dead volume (0.14 ml) of the flow-through cell 3, which is the balance of the inner volume of the flow-through cell 3 less the volume occupied by the sensors, plus the dead volume (0.17 ml) of the indwelling catheter 2.

The extent to which the response of the pH sensor 10A is reduced as a result of the adsorption of the blood substances was examined under conditions in which, while the flow velocity v3 during the length of time t3 was maintained equal to 0.5 times the flow velocity v2 during the length of time t2, that is, $v3=0.5 \cdot v2$, the flow velocity v2 was adjusted within the range of 0.06 to 2.00 milliliters per minute. The ratio of the value of an amplitude MS1, taken 5 hours subsequent to the start of the measurement, relative to the value of the amplitude MS1 taken at the time of start of the measurement, wherein said amplitude MS1 is taken when the time divider i of the response curve VS(i) exhibited by the pH sensor after the temperature compensation has been effected is equal to 1 and is represented by $[MS1=VS(1)+BS(1)]$ as shown in FIG. 5, was deemed as a parameter indicative of the extent of reduction in response of the pH sensor 10A. During this experiment conducted to examine the extent of reduction in response of the the pH sensor, the respiratory rate of a respirator attached to a dog was controlled to maintain the pH value of the dog arterial blood within the range of $7.45 \pm 0.05$, and, as the physiologically compatible solution infused to the dog, a mixture of 20,000 units of heparin per liter with the Ringer's solution containing lactic acid was used. Results of the experiment are tabulated in Table 1 below.

TABLE 1

| v2 ml/min | QF ml/min | q ml/min | f | MS1(5 hrs)/MS1(0 hr) |
|---|---|---|---|---|
| 0.06 | 0.41 | 0.013 | 1.5 | 0.63 |
| 0.12 | 0.82 | 0.054 | 3.0 | 0.65 |
| 0.16 | 1.12 | 0.084 | 4.0 | 0.83 |
| 0.18 | 1.23 | 0.095 | 4.5 | 0.85 |
| 0.25 | 1.71 | 0.143 | 6.0 | 0.88 |
| 0.42 | 2.80 | 0.252 | 10.0 | 0.91 |
| 0.82 | 5.60 | 0.532 | 20.0 | 0.94 |
| 1.23 | 8.40 | 0.812 | 30.0 | 0.96 |
| 1.64 | 11.20 | 1.09 | 40.0 | 0.96 |

As can be understood from Table 1 above, it is clear that the reduction in response of the pH sensor 10A could be suppressed effectively when f, i.e., the ratio of the positive flow volume relative to the reverse flow volume, is greater than 4. The greater the ratio f, the more minimized the reduction in response of the pH sensor 10A. However, if the ratio f is greater than 30, the minimization of the reduction in response of the pH sensor is saturated, and therefore, it is preferred that the monitoring apparatus is operated with the ratio f equal to or greater than 4 and, at the same time, equal or less than 30, that is, $4 \leq f \leq 30$ in order to suppress the adsorption of the blood substances to the sensor, particularly the pH sensor 10A.

Table 1 also indicates that, when the flow-through cell is used and when the ratio f is equal to or greater than 20, the infusing velocity q of the physiologically compatible solution exceeds 0.347 milliliter per minute which is the upper limit preferred from the clinical view point. In such case, as can be readily understood from the equation (4) discussed hereinbefore, the necessity arises to reduce the dead volume of the flow-through cell to reduce the reverse flow volume QR thereby to reduce the flow velocity of the transfusion pump. However, in view of the technical limitations existing on the minimization of the multi-chemical responsive sensor assembly and the flow-through cell and also on the reduction in flow velocity of the transfusion pump, the ratio f greater than 30 cannot be recommended. The reduction in response resulting from the adsorption of protein is generally considerable with the pH sensor, and the selection of the ratio f within the range of 4 to 30 does not pose any problem with the response of any one of the other sensors, that is, $PCO_2$ and $PO_2$ sensors used together with the pH sensor.

While the parameters q, tR and f used in the equation (4) defining the operating program for the transfusion pump have been determined in the manner as hereinbefore discussed with particular regards paid to the clinical requirements, the applicability of the chemical responsive sensor assembly in terms of the response characteristics thereof must also be taken into consideration. Since the illustrated pH, $PCO_2$ and $PO_2$ monitoring apparatus makes use of the pH and gas sensors which have different response characteristics, the determination of the operating program acceptable and applicable to all of the sensors used requires a careful consideration. This will now be illustrated by way of the response characteristic of the pH sensor.

The pH value of the Ringer's solution containing lactic acid used as the physiologically compatible transfusion solution during the experiment is about 6.5 while that of the dog's arterial blood is about 7.5. On the other hand, since the source potential of the pH-ISFET decreases with the increase of the pH value, it occurs that the source potential thereof decreases, when the blood having a pH value higher than that of the physiologically compatible transfusion solution flows into the flow-through cell during the drive of the transfusion pump in the second direction, and restores to the original value when the transfusion pump being driven in the second direction is switched to be driven in the first direction, giving a response curve as shown in FIG. 5.

Since the pH sensor is one type of ion sensitive sensor, the response time of the sensor itself is not greater than 1 second and is sufficiently small as compared with the length of time tR (for example, 0.67 minute) during which the transfusion pump is driven to extract the blood. Accordingly, as soon as the blood is supplied into the flow-through cell as a result of the drive of the transfusion pump in the second direction, an output from the pH sensor quickly reaches a value corresponding to the pH value of the blood as indicated by a portion, shown by the broken line in FIG. 5, of the response curve exhibited by the pH sensor during a period of time from the timing 0 to the timing tR. Since at a point of time indicated by VS(1), that is, at the end of the period during which the transfusion pump has been driven in the second direction, a sufficient contact between the blood and the pH sensor takes place, the reading VS(1) at this point of time can be regarded representing the source potential of the pH-ISFET (forming a part of the pH sensor) appropriate to the pH value of the blood so supplied into the flow-through cell.

Unexpectedly, it has however, been found that, for a certain period of time after the blood once supplied into the flow-through cell has returned from the flow-through cell to the blood vessel as a result of the switched drive of the transfusion pump in the first direction opposite to the second direction, the output from the pH sensor does not reach a value appropriate to the pH value of the physiologically compatible transfusion (the Ringer's solution containing lactic acid) so quickly as that exhibited during the length of time between the timing 0 and the timing tR in connection with the pH value of the blood. More specifically, as shown in FIG. 5, subsequent to the point of time VS(1), the source potential has fluctuated in such a way as to decrease to a value corresponding to a higher pH value and, after having reached a minimum value then slowly increased to a value corresponding to the pH value of the transfusion solution. Although the cause of this fluctuation has not yet been revealed sufficiently, it is suspected that the fluctuation would have resulted from the fact that, as a result of diffusion of $CO_2$ gas then dissolved in the blood, as well as bicarbonate ions into the transfusion solution when the blood and the transfusion solution are mixed together, the respective pH values of the blood and the transfusion solution at the interface therebetween are changed. In any event, it is usual for the pH sensor, which has been used to measure the pH value of the blood, to take an unexpectedly long time before it gives an output indicative of the pH value of the transfusion solution then superseding the blood. Because of this, it is preferred that the length of time tF during which the transfusion pump is driven in the first direction is within the range of 3 to 20 minutes, preferably within the range of 6 to 15 minutes.

On the other hand, with respect to the $PCO_2$ sensor, a 90% response time of the bare sensor, that is, the time at which the sensor output attains to 90% of the final output, ranges from 0.5 to 2 minutes which is longer than that of the pH sensor. Accordingly, where the length of time from the timing 0 to the timing tR is short, for example, 0.67 minute such as the illustrated instance, the $PCO_2$ sensor exhibits such a response curve as shown in terms of change in source potential of the pH-ISFET forming a part of the $PCO_2$ sensor in FIG. 5. As shown in FIG. 5, for a certain length of time subsequent to the start of drive of the transfusion pump in the second direction, the source potential of the $PCO_2$ sensor increases, reaches a maximum value and gradually decreases after it has reached a maximum value at a timing subsequent to the timing tR. Accordingly, for the reason similar to that discussed above in connection with the response curve of the pH sensor, the length of time during which the transfusion pump is driven in the first direction is preferred to be within the range of 3 to 20 minutes, preferably 6 to 15 minutes in order for the $PCO_2$ sensor to give a stabilized output faithful to the reading of the concentration of $PCO_2$ contained in the blood.

Similarly, with respect to the po sensor, a 90% response time of the bare sensor, ranges from 10 to 30 seconds which is smaller than that of the pH sensor. Accordingly, for a similar reason, the length of time during which the transfusion pump is driven in the first direction is preferred to be within the range of 1 to 20 minutes, preferably within the range of 2 to 10 minutes.

In general, however, with an increase in the length of time during which the transfusion pump is driven in the first direction, the amount of infusion of the physiologically compatible transfusion solution increases accompanied by increase of the cycle of measurement, and this is not desirable from the clinical standpoint. On the other hand, considering the response characteristics of the numerous sensors used and the purpose of substantially avoiding the adsorption of the blood substances discussed with the aid of Table 1, the longer length of time during which the transfusion pump is driven in the first direction is desirable. In order for these contradictory requirements to be satisfied, a compromise is made to render the flow velocity of the transfusion pump during the drive thereof in the first direction to be variable. In accordance with this compromise, as shown in FIG. 5, the transfusion pump is operated in such a way as to exhibit the flow velocity v2 during the first half of the length of time tF, during which the transfusion pump is driven in the first direction, to be lower than the flow velocity v3 during the later half of the same length of time tF, thereby to minimize the amount of the transfusion solution to be infused into the living body as compared with that infused when the transfusion pump is operated so as to exhibit the flow velocity v2 throughout the entire length of time tF.

Function (C)

This function is exhibited by the representative temperature setting device 19 shown in FIG. 2.

It is generally well known that the concentration of any one of the blood substances is sensitive to a change in temperature, and so is the sensitivity, the zero point and the response speed of any one of the sensors. In other words, any one of the sensor has a temperature dependency and, therefore, the use of a constant temperature cell has been with no exception necessitated in the prior art blood component monitoring apparatuses so far known to the inventors of the present invention, in which a constant temperature cell has carried out the measurement of the concentration of any one of the blood substances.

In contrast to the prior art blood component monitoring apparatuses utilizing the constant temperature cell, the illustrated blood component monitoring apparatus according to the present invention makes use of the flow-through cell which does not require the use of any tubing and is coupled direct with the indwelling catheter to avoid any possible adverse influence which would be brought about when a change in property of the blood substances would occur in the otherwise used tubing. The capability of the direct coupling of the flow-through cell with the indwelling catheter means that the flow-through cell is utilizeable in the blood component monitoring apparatus according to the present invention should not be bulky in size, and the blood component monitoring apparatus according to the present invention therefore, has no substantial latitude in using the flow-through cell which incorporates a constant temperature bath or any other means for keeping the temperature constantly at a predetermined temperature.

In view of the foregoing, the inventors of the present invention, contrary to the commonplace practice, have decided to use the flow-through cell having no means for maintaining the temperature thereof at a required value, but having a temperature sensor built therein for providing temperature data representative of the temperature inside the detector 11, which temperature data is utilized for compensating for any temperature dependent change of each of the sensors used.

Referring again to FIG. 5, since the body temperature of a patient is normally about 37° C. and the temperature of the transfusion solution (Ringer's solution containing lactic acid) is usually equal to the room temperature, the temperature of the detector inside the flow-through cell varies as shown therein in such a manner as to increase during the length of time between the timing 0 and the timing tR as a result of the introduction of the blood into the flow-through cell and to subsequently decrease progressively during the length of time tF during which the transfusion pump is driven in the first direction with the transfusion solution infused to the blood vessel through the flow-through cell. In view of this change, it is difficult to predict exactly the temperature of the blood actually measured during each pumping cycle. Since as hereinbefore described the concentration of the blood substances varies with change in temperature, it is important to make available the temperature measured during each pumping cycle.

In view of the foregoing, the inventors of the present invention have introduced a concept of the "representative temperature" as a conveniently utilizeable parameter. More specifically, this representative temperature is a temperature determined for the purpose of convenience as representing the measured temperature during the measurement of the concentration of the blood substance under a varying temperature. It appears to be reasonable to choose as the representative temperature at the time one of the temperature values $T(1)$ to $T(n)$, shown in FIG. 5, which has attained at a timing at which the most significant contribution has been made to the determination of the amplitude of the response curve of each of the sensors. By way of example, in the case of the pH sensor, since $VS(1)$ can be considered as a balanced output indicative of the pH value of the blood, it is reasonable for the temperature $T(1)$ to be determined as the representative temperature. In the case of any one of the $PCO_2$ and $PO_2$ sensors, although the response time thereof is relatively long the maximum or minimum value of the output from the respective gas sensor occurs at a timing later than the timing $i=1$, the blood which is held in contact with the respective gas sensor at about a timing $i=1$ appears to have made the most significant contribution to the determination of the maximum or minimum output from the respective gas sensor. This is because, at the timing $i=1$, the respective gas sensor is deeply immersed in the blood being supplied into the flow-through cell and the temperature of the blood contacting the respective gas sensor at such timing is highest and because it can therefore be presumed that exchange of gas between the gas permeable membrane and the blood may be accelerated. In view of the foregoing considerations, the temperature $T(1)$ was taken as the representative temperature applicable to all of the pH, $PCO_2$ and $PO_2$ sensors used. According to the experiments conducted, the temperature $T(1)$ was 32° C.

It is, however, to be noted that the representative temperature used in the practice of the present invention may not be always limited to the specific value, that is, 32° C., but may be chosen on case-by-case basis.

Function (D)

This function is exhibited by the temperature compensating device 20 and the correcting device 21 shown in FIG. 2. This function will now be described as incorporated in the pH, $PCO_2$ and $PO_2$ monitoring apparatus now under discussion.

Let it be assumed that the source potential of the pH sensor before the compensation for temperature dependent change is effected is $VSo(i)$, the source potential of the $PCO_2$ sensor before the compensation for temperature dependent change is effected is $VCo(i)$, and the reducing current of the $PO_2$ sensor before the compensation for temperature dependent change is effected is $VRo(i)$, wherein i represents a positive integer, 1, 2, 3 . . . n-1 and n. In order to convert respective unprocessed outputs from these sensors into the associated outputs $VS(i)$, $VC(i)$ and $VR(i)$ all occurring at the representative temperature $T(1)$, information should be made available of the temperature dependent characteristics of these sensors. As hereinbefore discussed, the source potential of each of the pH-ISFETs for the pH and $PCO_2$ sensors exhibits a linear proportional relationship with temperature at a low drain current range. Also, the relative reducing current of the $PO_2$ sensor varies at a rate approximately proportional to the change in temperature. Hence, the following equations utilizeable to compensate for temperature dependent change can be obtained.

$$VS(i) = VSo(i) + TS \cdot \Delta T(i) \quad (5)$$

$$VC(i) = VCo(i) + TC \cdot \Delta T(i) \quad (6)$$

$$VR(i) = VRo(i) \cdot (1 + TR \cdot \Delta T(i)) \quad (7)$$

$$\Delta T(i) = T(1) - T(i) \quad (8)$$

wherein TS, TC and TR represent temperature coefficients of the respective outputs from the pH, $PCO_2$ and $PO_2$ sensors. The temperature coefficients TS and TC are normally within the range of 0.3 to 2.0 mV/°C., and the temperature coefficient TR is normally within the range of 0.02° to 0.06/° C. FIG. 5 also illustrates output curves VS, VC and VR representative of the respective converted outputs at the representative temperature T(1).

Then, it is necessary to determine the amplitude or an equivalent thereof, that is, a characteristic value based on the amplitude, from each of these output curves. Although numerous methods are possible to determine the amplitude, straight lines each drawn between the timing O and the timing tT as shown by the respective single-dotted chain line in FIG. 5 were used as respective base lines BS, BC and BR. The amplitude MS1 of the output from the pH sensor was represented by the balance between VS(1) and BS(1). That is, $$MS1 = VS(1) - BS(1) \quad (9)$$

The amplitude MC1 of the output from the $PCO_2$ sensor was represented by the balance between the maximum value VC(KC) of VC(i) and a value BC(KC) on the base line BC at which the maximum value VC(KC) has been exhibited. That is, $$MC1 = VC(KC) - BC(KC) \quad (10)$$

Similarly, with respect to the amplitude of the output from the $PO_2$ sensor, a value MR1 represented by the ratio of the maximum value VR(KR) of VR(i) relative to a value BR(KR) on the base line BR at which the maximum value VR(KR) has been exhibited was taken as an equivalent of the amplitude thereof. That is, $$MR1 = VR(KR)/BR(KR) \quad (11)$$

The reason for the employment of the ratio as the equivalent of the amplitude instead of the employment of the balance between VR(KR) and BR(KR) in the determination of the amplitude of the output from the $PO_2$ sensor is that any deviation in amplitude among the respective outputs from the sensors can be minimized. In other words, the base line value BR for the $PO_2$ sensor (the value of the reduction current corresponding to lactate Ringer equilibrated to room air) varies from one sensor to another and, therefore, if the amplitude represented by the balance between VR and BR is employed, deviation among the sensors would become manifested. In view of this, the employment of the ratio as the equivalent of the amplitude is effective to avoid any possible influence which would be brought about when the sensitivity of the $PO_2$ sensor is lowered during the measurement conducted for a prolonged period of time.

Thereafter, with the use of the amplitudes and the equivalent of the amplitude, that is, the characteristic values, as hereinbefore described, the respective concentrations of the blood substances of interest at the representative temperature are determined. It is a correction equation that coordinates the magnitude of each amplitude with the concentration of the associated blood substance of interest, the following correction equations being used in the practice of the present invention in association with the respective pH, $PCO_2$ and $PO_2$ sensors.

$$pH = a \cdot MS1 + b \quad (12)$$
$$PCO_2 = MC1 \cdot 10^{(c \cdot MC1^2 + d \cdot MC1 + e)} \quad (13)$$
$$PO_2 = f \cdot MR1 \quad (14)$$

wherein a, b, c, e and f represent constants peculiar to the respective sensors at the representative temperature T(1) and depend on temperature as will be discussed later.

These correction equations were obtained after an extensive study of the relationship between the amplitudes of the outputs from the respective sensors and the concentrations of the blood substances of interest. With respect to the pH sensor, a linear proportional relationship can be found between the amplitude MS1 and the pH value of the blood. Also, a positive proportional relationship can be found between the equivalent MR1 of the amplitude in the output from the $PO_2$ sensor and the partial pressure of oxygen contained in the blood. The correction equation (13) associated with the $PCO_2$ was first formulated by the inventors of the present invention and is disclosed in the Japanese Patent application No. 59-27852 applied for a patent in Japan in 1984.

The constants peculiar to the respective sensors, which are used in the correction equations (12) to (14), should be made available at the start of the measurement. For this purpose, use has been made of a control solution containing known concentrations of chemical substances and then the constants peculiar to the respective sensors are determined in reference to the relationship between the known concentrations of the chemical substances in the respective control solution and the amplitudes. Generally, in order for the constants to be determined, the control solutions equal in number to the number of the constants required to be determined are necessary. Therefore, two control solutions are needed to determine the two constants peculiar to the pH sensor, three control solutions are needed to determine the three constants peculiar to the $PCO_2$ sensor, and one control solution is needed to determine the only constant peculiar to the $PO_2$ sensor.

In determination of the constants peculiar to the pH, $PCO_2$ and $PO_2$ sensors used in the apparatus according to the present invention, three types of aqueous solutions each similar in composition to that of blood plasma and containing 24 millimole per liter of sodium bicarbonate and 154 millimole per liter of salt, which solutions were saturated by injecting thereinto respective control gases of a mixture of 5% $CO_2$ and 5% $O_2$, a mixture of 10% $CO_2$ and 10% $O_2$ and a mixture of 20% $CO_2$ and 20% $O_2$, respectively, were used. In the practice of the present invention, two types of these control solutions were used for the determination of the constants a and b, all types of these control solutions were used for the determination of the constants c, d and e, and one type of these control solutions was used for the determination of the constant f.

It is to be noted that each of these constants a, b, c, d, e and f used in the previously mentioned equations (12) to (14) is affected by the measurement temperature. Accordingly, for the purpose of the present invention, before the final determination of each of the peculiar constants a to e and f, two values $a_{27}$, $a_{37}$; $b_{27}$, $b_{37}$; $c_{27}$, $c_{37}$; $d_{27}$, $d_{37}$; $e_{27}$, $e_{37}$; and $f_{27}$, $f_{37}$ for each constant a, b, c, d, e and f were determined at 27° C. and 37° C., respectively, and, then, each peculiar constant at the representative temperature T(1) was determined with the use of the following equation.

$$X_{T(1)} = X_{27} + (x_{37} - x_{27}) \cdot [(T(1)-27)/(37-27)] \quad (15)$$

x=a, b, c, d, e or f

Although it appears that the practice of the present invention is more or less complicated because values necessary for the determination of the constants a to e and f as well as the parameters TS, TC and TR used in the equations (5) to (7), arrangement can be made to render these specific values available from a supplier of the sensor assembly by the use of an automatic testing device operated by the supplier, so that the user of the apparatus of the present invention can do a job of inputting these values into the central processor.

Function (E)

This function is exhibited by the adjusting device 22.

In view of the foregoing discussion, the calculation performed by the use of the bare outputs from the various sensors and the constants peculiar to these sensors and by the use of the equations (5) to (12) should give rise to the concentration and the partial pressure of the blood substances. However, as a result of experiment conducted on animals, it has been found that, for given test material, the measurements obtained by the use of the apparatus according to the present invention differ from those obtained by the use of a commercially available IL meter (an automatic blood gas chromatographic analyzer, System 1303), particularly in respect of the pH value and the concentration of PO₂, as illustrated in Table 2 below.

TABLE 2

|  | Apparatus of Invention | IL Meter System 1303 |
|---|---|---|
| pH | 7.286 | 7.459 |
| PCO$_2$ (mmHg) | 31.1 | 29.1 |
| PO$_2$ (mmHg) | 83.6 | 111.3 |

Comparison tests carried out to obtain the result tabulated in Table 2 above were conducted using v2=0.42 milliliter per minute and using the same conditions as used to obtain the results tabulated in Table 1. The results illustrated in Table 2 were obtained 40 minutes after the start of monitoring. While the results associated with the the use of the IL meter were based on the measurement carried out using a constant temperature bath maintained at 37° C., those associated with the present invention were based on the measurement carried out using the representative temperature T(1) of 32° C. Therefore, in listing the specific values in Table 2 for the purpose of comparison with those values given by the IL meter, the actually measured values by the IL meter were converted by the use of the following equations (16) to (18) to give the comparative values at 32° C. It is, however, to be noted that the following conversion equations are disclosed by E. R. Ashwood et al, in Clinical Chemistry No. 29, p. 1877 (1983).

$$pH_{37} = pH - 0.0146(t-37) \quad (16)$$

$$\log (PCO_2)_{37} = \log (PCO_2)_t + 0.019(37-t) \quad (17)$$

$$\log (PO_2)_{37} = \log (PO_2)_t + [(37-t)/2.303] \cdot$$
$$[0.058/\{0.243 \cdot ((PO_2)t/100)^{3.88} + 1\}] + 0.013$$

wherein t represents the representative temperature T(1).

As is clear from Table 2, the differences between the pH value and the concentration of PO₂ measured by the apparatus of the present invention and those by the IL meter, respectively, are relatively large. Study has indicated that the differences resulted from the constants peculiar to the sensors used, which were determined with the use of the control solutions as discussed in connection with the function (D), and do not apply to the measurement of the blood substances. It appears that, so far as the absence or presence of protein components participating in the equilibrium of the pH value, those of hemoglobin participating in the equilibrium of the PO₂ concentration, and the difference in viscosity are concerned, there is a vast difference between the blood and the control solution even though the latter is prepared to provide an analog of blood, which would have resulted in the above discussed differences in the results of measurement carried out with the use of apparatus of the present invention and the commercially available IL meter.

Although the determination of the constants peculiar to the sensors used with the use of blood would be a practical solution, this method cannot be employed without difficulty because of problems associated with contamination of the sensors and handling procedures. As an alternative method, the inventors of the present invention have, as a result of examination, found that the use of amplitude correcting parameters would be a reasonable solution. In other words, the inventors of the present invention have made it a practice to use theoretically calculated amplitudes MS2, MC2 and MR2, calculated by the following equations (19) to (21), in place of the actually measured amplitudes MS1, MC1 and MR1.

$$MS2 = MS1 + XS \quad (19)$$
$$MC2 = MC1 \cdot XC \quad (20)$$
$$MR2 = MR1 \cdot XR \quad (21)$$

wherein XS, XC and XR represent the respective amplitude correcting parameters. Depending on the type of sensors, the theoretically calculated amplitude may represent the sum of the amplitude correcting parameter and the actually measured amplitude such as in the equation (19) or the product of the both such as in each of the equations (20) and (21), and during the course of experiments conducted with a view to developing the apparatus according to the present invention, the use of the sum of the amplitude correcting parameter and the actually measured amplitude so far associated with the pH sensor and the use of the product of the both so far associated with any one of the PCO₂ and PO₂ sensors were found to be advantageous in that a single correcting parameter can be used for a relatively wide range of measurements.

Specific values of these correcting parameters have been found within the following ranges as a result of experimental measurements carried out by the use of the apparatus according to the present invention as supported by the use of the commercially available IL meter.

XS = −5 to −40 mV, and −20 to −30 mV in most cases.
XC = 0.5 to 1.4, and 0.9 to 1.1 in most cases.

-continued

XR = 0.5 to 1.5, and 0.7 to 1.3 in most cases.

For each of these correcting parameters, a specific value falling within the above mentioned range or any empirically predetermined value may be employed. However, in order to determine the respective specific values as accurately as possible, a recommended method is to measure MS1, MC1 and MR1 associated with blood of interest with the use of the apparatus according to the present invention and, at the same time, to measure the pH value and the concentrations of $PCO_2$ and $PO_2$ of the same blood of interest with the use of an analyzer, for example, the commercially available IL meter separate from the apparatus according to the present invention, followed by the calculation using the previously discussed equations (12) to (14) and (19) to (21) and the following equations (22) and (23).

$$XS = (pH^* - b)a - MS1 \quad (22)$$

$$XR = PO_2^*/(f \cdot MR1) \quad (23)$$

wherein pH* and $PO_2^*$ represent, respectively, the pH and $PO_2$ values measured by the use of the IL meters and converted according to the associated equations to provide the values at the representative temperature T(1). With respect to the parameter XC, a quantity XXC is introduced, and the right-hand term of the equation (13) wherein, in place of MC1, $MC2 = MC1 \cdot XXC$ is used while the quantity XXC is changed within the range of 0 to 2.0 at predetermined intervals, for example, 0.01, solved. One of the calculated quantities XXC, which approximates to the $PCO_2^*$ value representing the PCO2 value measured by the use of IL meter and converted according to the associated equations to provide the value at the representative temperature T(1), is taken as the correcting parameter XC.

These correcting parameters XS, XC and XR are calculated based on the amplitudes measured during the first or second cycle of measurement, and once they have been fixed, the once-fixed correcting parameters XS, XC and XR can be effectively used for about 10 to about 50 hours with no noticeable reduction in measurement accuracy being accompanied. However, the prolonged measurement in excess of about 50 hours would result in a change in characteristic of the sensors as a result of adsorption of protein or any other substances, accompanied by increase in the magnitude of measurement errors. Therefore, the correcting parameters XS, XC and XR should be updated by measuring the accurate concentrations of the chemical substances contained in blood with the use of the different apparatus such as, for example, the commercially available IL meter and then by following the previously discussed procedures, so that the measurement can be continued for an extra length of time within the range of about 10 to about 50 hours. Thus, the correcting parameters XS, XC and XR are extremely useful parameters which can be used not only to compensate for the measurement error resulting from the difference between the control solution and the actual blood, but also to correct any possible measurement error resulting from a change in characteristics of the individual sensors during the actual measurement.

While the numerous features available in the apparatus according to the present invention have been discussed, the apparatus according to the present invention operates in a manner which will now be described with particular reference to FIG. 6 illustrating a flow chart showing the sequence of operation thereof. Although the illustrated flow chart starts with the inputting of the peculiar constants, the temperature coefficients and the correcting parameters and ends with the calculation of the concentrations of the blood chemical substances of interest at the representative temperature T(1), an additional step for performing the conversion according to the equations (16) to (18) may be added where the measured values are desired to be converted into respective values at 37° C.

Referring now to FIG. 6, at step S1, the peculiar constants $a_{27}$ to $f_{27}$ and $a_{37}$ to $f_{37}$, and the temperature coefficients TS, TS and TR all associated with the sensors used in the apparatus according to the present invention are inputted together with the initial values XSo, XCo and XRo of the respective correcting parameters XS, XC and XR. The initial correcting parameters XSo, XCo and XRo are values selected from the previously mentioned ranges of $-20$ to $-30$ mV, 0.9 to 1.1, and 0.7 to 1.3.

| pH: $a_{27}$, $a_{37}$, $b_{27}$, $b_{37}$ | TS | XSo |
| PCO2: $c_{27}$, $c_{37}$, $d_{27}$, $d_{37}$, $e_{27}$, $e_{37}$ | TC | XCo |
| PO2: $f_{27}$, $f_{37}$ | TR | XRo |

At subsequent step S2, a start button is depressed to cause the transfusion pump to be driven in the second direction for the length of time tR. After the passage of the length of time tR, driving of the transfusion pump in the first direction opposite to the second direction is automatically initiated at step S3 and continues for the length of time tF. During this length of time tF, and at step S4, the outputs from the respective sensors are read out the n-number of times at intervals of tF/n.

| Temperature sensor: | T(i) |
| pH sensor: | VSo(i) |
| PCO2 sensor: | VCo(i) |
| PO2 sensor: | VRo(i) |
| | i = 1~n |

Thereafter, and at step S5, the transfusion pump is reversed so as to be driven in the second direction for the length of time tR. During this length of time tR, and at step S6, the following data processing is carried out.

6-1: To determine the representative temperature T(1).

6-2: To determine the constants peculiar to the respective sensors according to the equation (15).

$$x_{T(1)} = x_{27} + (x_{37} - x_{27}) \cdot [(T(1) - 27)/(37 - 27)] \quad (15)$$

x = a, b, c, d, e or f 6-3: To convert the respective outputs from the sensor elements into values appropriate at the representative temperature T(1) according to the associated equations (5) to (8).

$$VS(i) = VSo(i) + TS \cdot \Delta T(i) \quad (5)$$

$$VC(i) = VCo(i) + TC \cdot \Delta T(i) \quad (6)$$

$$VR(i) = VRo(i) \cdot (1 + TR \cdot \Delta T(i)) \quad (7)$$

$$\Delta T(i) = T(1) - T(i) \quad (8)$$

6-4: To calculate characteristic values (amplitudes or values equivalent thereof) of the converted curves according to the equations (9) to (11).

$$MS1 = VS(1) - BS(1) \quad (9)$$

$$MC1 = VC(KC) - BC(KC) \quad (10)$$

$$MR1 = VR(KR)/BR(KR) \quad (11)$$

6-5: To correct the amplitudes with the use of the initial correcting parameters XSo, XCo and XRo, inputted at step S1, according to the equations (19) to (21).

$$MS2 = MS1 + XSo \quad (19)$$

$$MC2 = MC1 \cdot XCo \quad (20)$$

$$MR2 = MR1 \cdot XRo \quad (21)$$

6-6: To calculate the chemical concentrations predominant at the representative temperature $T(1)$ with the use of the corrected amplitudes according to the following equations (12A) to (14A).

$$pH = a \cdot MS2 + b \quad (12A)$$
$$PCO_2 = MC2 \cdot 10^{(c \cdot MC2^2 + d \cdot MC2 + e)} \quad (13A)$$
$$PO_2 = f \cdot MR2 \quad (14A)$$

At step S7, a decision is made to determine whether or not the correctng parameters XS, XC and XR are to be determined. This decision is carried out when, for example, an external push button is manipulated by an operator of the apparatus. If the use of the initial correcting parameters XSo, SCo and XRo poses no problem and are therefore satisfactory, the result of decision at step S7 should be given "No", allowing the program to return to step S3. However, if the result of decision at step S7 is given "Yes", the program proceeds to step S8 at which the transfusion pump is driven in the first direction for the length of time tF so that, during this length of time tF and at step S9, the correcting parameters can be updated by inputting the values measured by the separate apparatus, for example, the commercially available IL meter and then calculating according to the following equations (22), (23) and, also, the correcting parameter XC can be calculated to satisfy the following equation (13A).

$$XS = (pH^* - b)a - MS1 \quad (22)$$

$$XR = PO_2^*/(f \cdot MR1) \quad (23)$$

$$PCO_2^* = MC1 \cdot XC \cdot 10^{[c \cdot (MC1 \cdot XC)^2 + d \cdot MC1 \cdot XC + 3]} \quad (13A)$$

After the calculation at step S9, the program returns to step S5 to repeat the sequence from step S5 to step 7. Unless the chemical concentrations measured at step S6 during the previous cycle depart largely from those measured with the use of the separate apparatus, "No" has to be selected as a result of current decision at step S7, but should they depart largely from the values measured with the use of the separate apparatus, "Yes" has to be selected so that, at succeeding steps S8 and S9, the correcting parameters can be again calculated.

Figure 7:
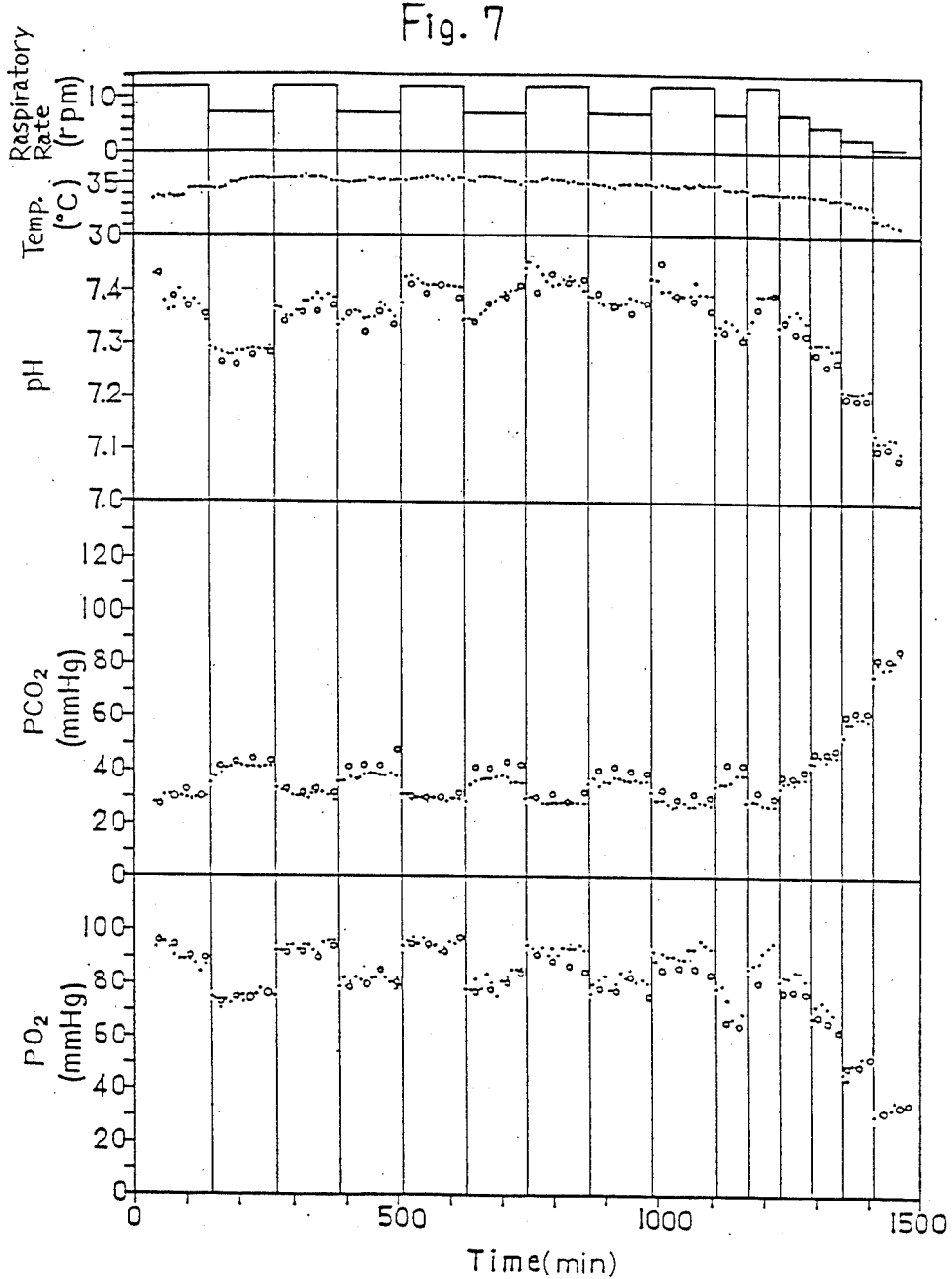
FIG. 7 is a graph showing a result of measurement of pH, $PCO_2$ and $PO_2$ of dog blood.

FIG. 7 illustrates a graph showing the pH, $PCO_2$ and $PO_2$ measurements of the dog's arterial blood which were plotted by the use of the pH, $PCO_2$ and $PO_2$ monitoring apparatus of the transfusion type according to the present invention wherein all of the functions (A) to (E) are incorporated. Values represented by the plots in the graph of FIG. 7 are those converted with the use of the equations (16) to (18) to provide the values at 37° C. For the purpose of comparison, the corresponding values obtained from the same blood by the use of the commercially available IL meter, System 1303 are indicated by the respective circles in the graph of FIG. 7. Conditions under which both of the apparatuses, that is, the apparatus according to the present invention and the commercially available IL meter were operated are identical with those which were used to give the results tabulated in Table 1. During the experiment, the dog was aspirated with the aspiratory rate varied at a predetermined interval and finally progressively down to zero as indicated at top of the graph of FIG. 7.

The graph of FIG. 7 has made it clear that the measurement carried out with the use of the apparatus according to the present invention substantially matches that carried out with the commercially available IL meter for a substantially prolonged period of time. Attention is called to the fact that, for the purpose of this experiment, the use of the IL meter has necessitated the extraction of 51 samples of 3 milliliter of blood from the dog totaling to 153 milliliters, posing a potential problem associated with the loss of blood and the complicated and time-consuming blood extracting procedures. In contrast thereto, with the apparatus of the present invention, no loss of blood has occurred and, rather, no blood is needed to be extracted, but instead only flows into the flow-through cell and then back to the blood vessel.

Hereinafter, results of clinical tests conducted with the use of the pH, $PCO_2$ and $PO_2$ monitoring apparatus of the transfusion type according to the present invention, which is similar to that used during the above described test with the dog and in which all of the functions (A) to (E) are incorporated, will be described.

As a matter of course, before the clinical tests were conducted, not only the physical safety, but also the biological safety of the apparatus according to the present invention had been confirmed and, in addition, the reliability of the apparatus had also been confirmed. Conditions under which the apparatus was operated were substantially identical with those used during the test with the dog.

Figure 8:
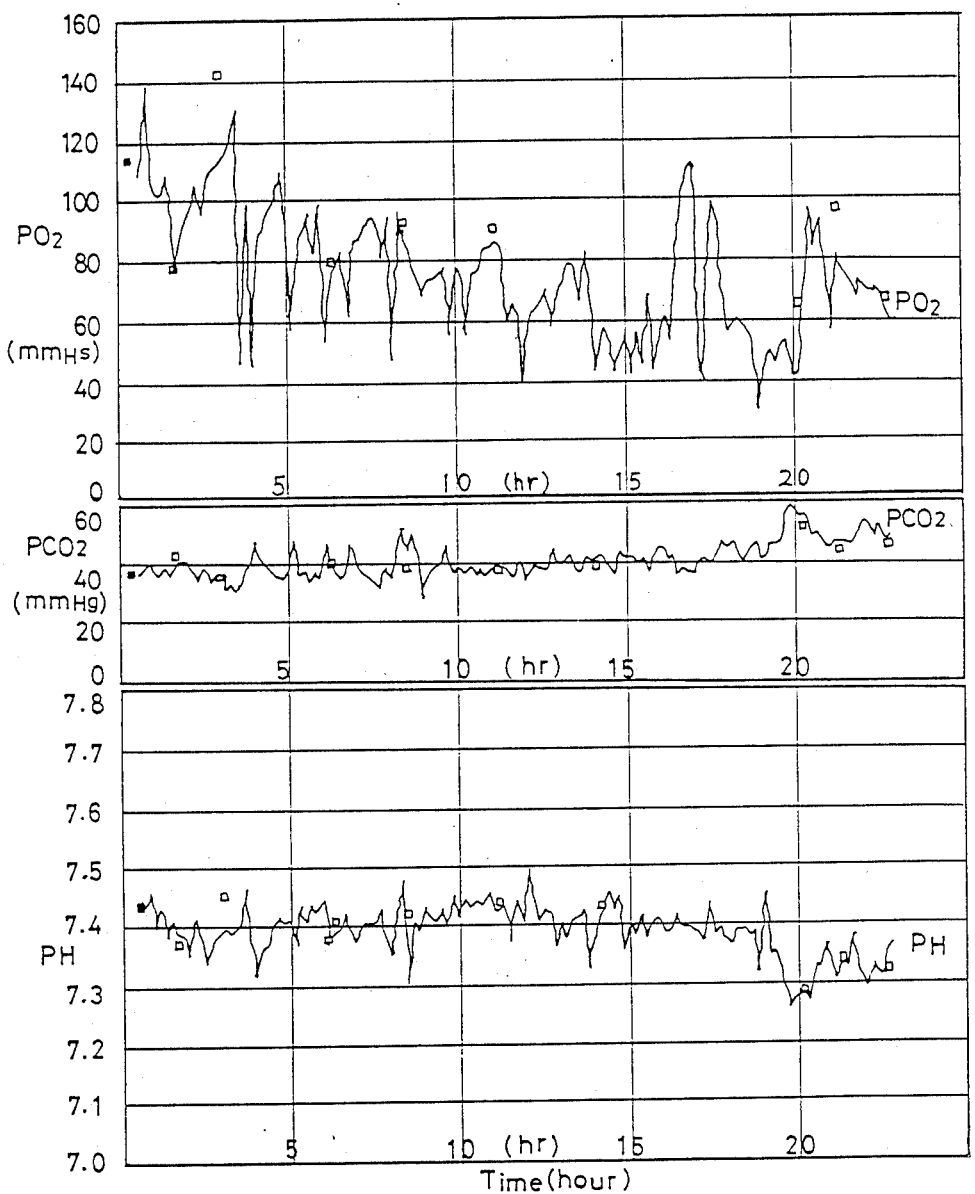
FIGS. 8 and 9 are graphs showing respective clinical test results.

Clinical Test 1:

In FIG. 8, a monitoring chart is shown in which the results of measurement of $PO_2$, $PCO_2$ and pH of arterial blood of a patient being aspirated are illustrated. Each of the solid-lined curves shown in the graph of FIG. 8 is a line drawn so as to connect respective values measured with the use of the apparatus according to the present invention while each of the blank square markings plotted in the same graph represents respective values measured with the use of the commercially available IL meter. The black square markings represent the first $PO_2$, $PCO_2$ and pH values measured with the use of the IL meter which were used to determine the correcting parameters XS, XC and XR.

The patient examined clinically was medicinally poisoned accompanied by severe depression and, accordingly, the measurements according to the apparatus of the present invention show considerable fluctuations with the $PO_2$, $PCO_2$ and pH values exhibiting a correlation among each other in most cases. In other words, reduction of the $PO_2$ is accompanied by increase of the $PCO_2$ value and reduction of the pH value. Such a fluctuation is an indication characteristic of respiratory acidosis and, in fact, the patient developed respiratory acidosis one or two times in about an hour. In the worst case, the measured $PO_2$ value reached a critical value lower than 50 mmHg although for a relatively short length of time.

On the other hand, the extraction of blood from the patient for the measurement with the use of the commercially available IL meter cannot be executed so frequently and, therefore, during the clinical test, a single sample of blood was extracted at intervals of one to two hours. In view of this, it is difficult to timely detect the occurrence of the respiratory acidosis as evidenced by the fact that the actually measured $PO_2$ value with the IL meter represented values was higher than 65 mmHg at all times during the clinical test. The lung function of the patient in question would have been diagnosed normal if the examination were carried out by sampling and measuring blood occasionally such as with the use of the IL meter.

In any event, from the graph of FIG. 8, it is clear that the specific values measured with the use of the apparatus according to the present invention at the time when the blood was sampled and measured with the IL meter substantially match with those measured with the use of IL meter. Thus, the feature of continuous measurement with no need to discard the blood out of the system according to the present invention is effective to quickly and accurately grasp the condition of the case.

Figure 9:
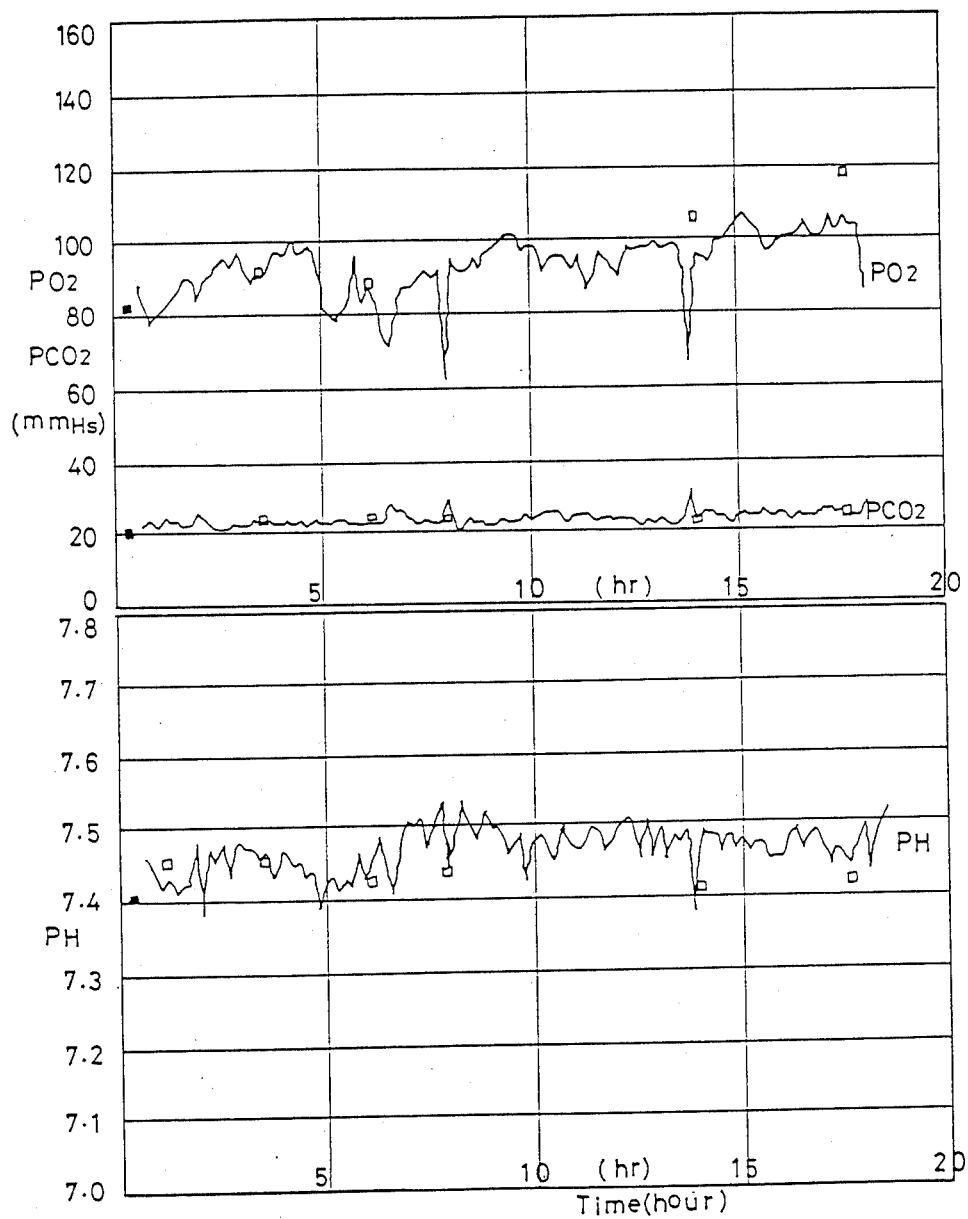

Clinical Test 2:

In FIG. 9, a monitoring chart is shown in which results of measurement of $PO_2$, $PCO_2$ and pH of arterial blood of another patient being aspirated are illustrated. The patient was a case with cerebral bleeding, but showed a normal lung function and, therefore, the measured values of $PO_2$, $PCO_2$ and pH were stable throughout the clinical test. Although respiratory acidosis occurred two times in about 8 hours and about 14 times subsequent to the start of the clinical test because the aspirator was removed at such timings for the removal of phlegm.

In any event, from the graph of FIG. 9, it is clear that the specific values measured with the use of the apparatus according to the present invention at the time when the blood was sampled and measured with the IL meter substantially match with those measured with the use of IL meter.

As the results of the clinical tests show, the apparatus according to the present invention has the following advantages and has been shown as effective and useful clinically.

(i) No substantial loss of blood is incurred.

(ii) The measurements match substantially with the measurements achieved by the blood sampling technique and, therefore, an accurate measurement of the blood substances is possible.

(iii) Since the apparatus according to the present invention is simple and compact in structure and relatively easy to handle, it is suited for use in situ and bedside.

The following embodiment of the present invention which will be subsequently described with reference to FIGS. 10 to 13 is the blood component monitoring apparatus designed to accomplish the first and second mentioned objects of the present invention.

As hereinbefore discussed, the reduction in response of the various sensors used in any monitoring apparatus of a type to which the present invention pertains is essential and necessary in order to accomplish an accurate measurement of chemical properties of blood substances. One method to achieve is to add the blood anti-coagulant such as heparin to the physiologically compatible transfusion solution as is embodied in the practice of the present invention.

However, most of the patients, whose blood is continuously monitored by the apparatus according to the present invention, are severely ill cases who have just received a surgical opreation and/or who are respirated and, therefore, it often happens that the amount of heparin added to the physiologically compatible transfusion solution, hence the amount of the transfusion solution being transfused, is required to be reduced as much as possible. Moreover, suffering children and patients with kidney disorder are restricted of water intake, and even with those cases, it is necessary to reduce the amount of the physiologically compatible transfusion solution to be transfused.

In view of the foregoing, and in view of the fact that the latter half of the physiologically compatible solution transfused to the patient's blood vessel is used mainly for the purpose of rinsing the sensors used in the blood component monitoring apparatus according to the foregoing embodiment and contains no substantial blood, the transfusion solution used to rinse the sensors need not be circulated back to the blood vessel. The apparatus according to the second preferred embodiment which will now be described is so designed as to drain the latter half of the transfusion solution out of the system thereby to reduce the amount of the transfusion solution being actually transfused into the blood vessel.

Figure 10:
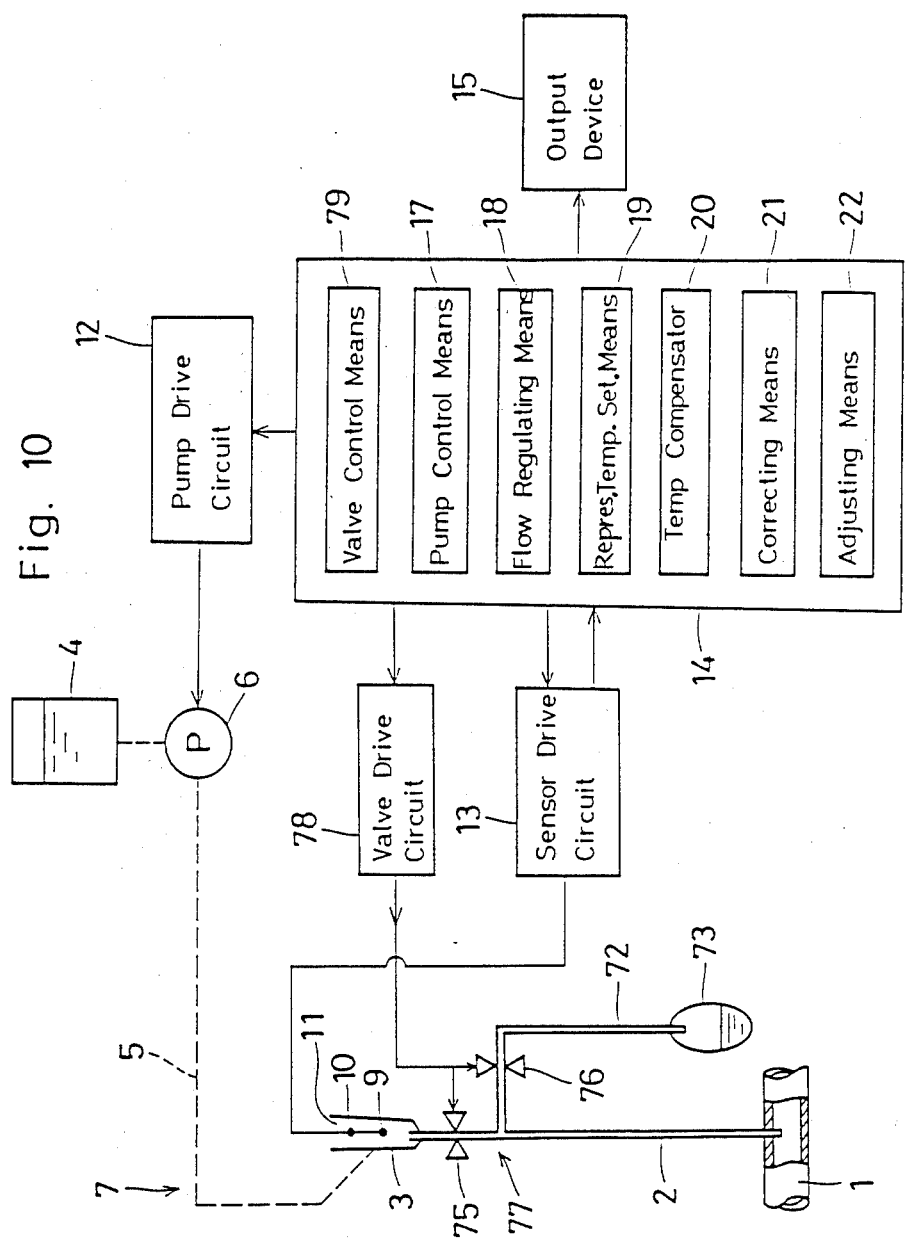
FIG. 10 is a diagram similar to FIG. 2, showing another preferred embodiment of the present invention.

Referring now to FIG. 10, the flow-through cell 3 has its tip fluid-connected with the blood vessel 1 through the indwelling catheter 2 made of synthetic resin. A portion of the indwelling catheter 2 between the blood vessel 1 and the flow-through cell 3 is fluid-connected with a drain tube 72 leading to a drain container 73 for collecting the drained transfusion solution. Another portion of the indwelling catheter 2 which is upstream of the junction between the indwelling catheter 2 and the drain tube 72 with respect to the flow-through cell 3 is provided with an electromagnetically operated blood valve 75, and a similar drain valve 76 is also disposed on the drain tube 72. While the blood and drain valves 75 and 76 altogether constitute a valve device 77, each of these valves 75 and 76 is preferably of a design operable to selectively pinch and release the associated catheter or drain tube externally to close and open, respectively, by means of an electromagnetic actuator. As will become clear from the subsequent description, the blood and drain valves 75 and 76 are operated in an opposed sense relative to each other. In other words when one of the blood and drain valves 75 and 76 is closed, the other of the blood and drain valves 75 and 76 is opened. The valve device 77 is electrically connected with a valve drive circuit 78 adapted to be controlled by a valve control means 79 incorporated in the central processor 14.

Figure 11:
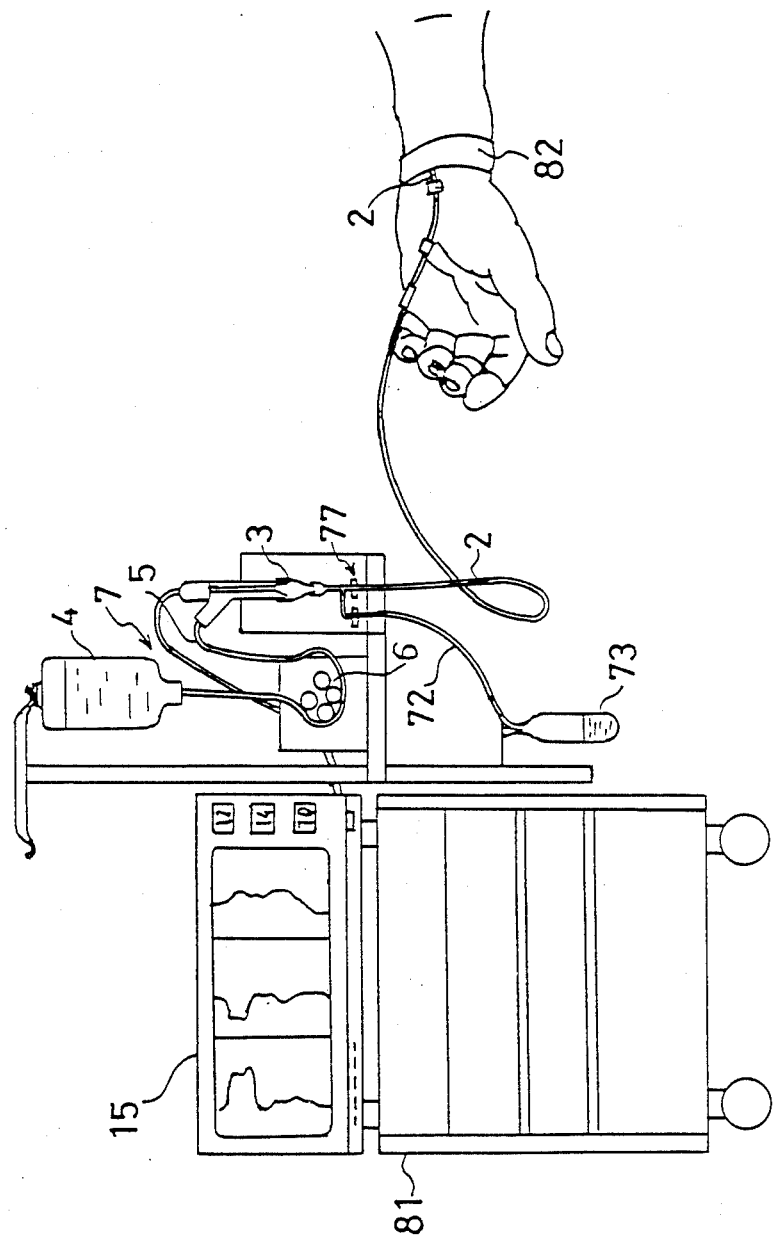
FIG. 11 is a schematic front elevational view illustrating a machine set-up of the blood component monitoring apparatus according to such another preferred embodiment of the present invention.

The machine layout of the blood monitoring apparatus according to the second preferred embodiment of the present invention is illustrated in FIG. 11. All of the transfusion device 7 including the flow-through cell 3 and the transfusion pump 6 comprised of, for example, a roller pump, the output device 15, the drain container 73, the valve device 77 and the other solid machine components are mounted on a wheeled carriage 81 so that the apparatus as a whole can be brought bedside. When in use for the blood measurement, the tip of the indwelling catheter 2 is punctured into the blood vessel 5 of the patient and then fixed in position by the use of a band 82.

Figure 12:
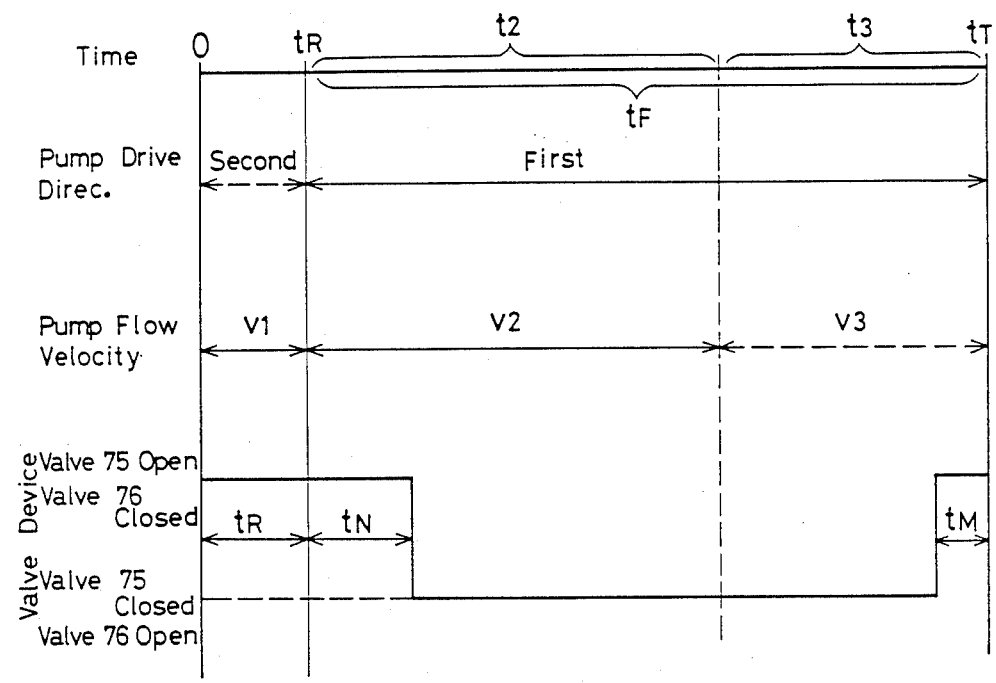
FIG. 12 is a timing chart showing a program used to control valves used in the blood component monitoring apparatus according to the embodiment of FIG. 10.

The valve control means 79 controls the valve drive circuit 78 according to a predetermined program to alternately close and open the blood and drain valves 75 and 76 forming the valve device 77, an example of the control according to such predetermined program is shown in FIG. 12.

Referring to FIG. 12 in combination with FIG. 10, the valve device 77 can assume one of two different states; a first state in which the blood and drain valves 75 and 76 are opened and closed, respectively, and a second state in which the blood and drain valves 75 and 76 are closed and opened, respectively. The valve device 77 can be rendered to assume the first state in readiness for the blood extraction a predetermined time tM prior to the timing tT at which the drive of the transfusion pump in the first direction is terminated (that is, the timing of start of drive of the transfusion pump in the second direction) and is maintained in the first state during a period of time which is the sum of the length of time tR, during which the transfusion pump 6 is driven in the second direction, and the succeeding length of time tN subsequent to the start of drive of the transfusion pump 6 in the first direction. During the length of time tR, the blood is extracted into the flow-through cell 3 through the catheter 2, and during the subsequent length of time tN the blood once extracted into the flow-through cell 3 is returned to the blood vessel together with the transfusion solution through the catheter 2. However, when the predetermined time tN has passed during the drive of the transfusion pump 6 in the first direction, that is, when the positive flow volume subsequent to the start of drive of the transfusion pump 6 in the first direction has attained a predetermined value, the the valve device 77 is caused to assume the second state so that the transfusion solution remaining in the flow-through cell 3 can be drained to the drain container 73 through the drain tube 72.

Since the blood once drawn into the flow-through cell 3 during the drive of the transfusion pump 6 in the second direction is, according to the present invention, required to be returned to the blood vessel 1 by the drive of the transfusion pump 6 in the first direction, the predetermined amount of a mixture of the blood to be returned to the blood vessel 1 and the transfusion solution to be transfused into the blood vessel 1 must be greater than the amount of the blood once drawn into the flow-through cell 3 during the drive of the transfusion pump 6 in the second direction. Accordingly, when the reverse flow velocity and the positive flow velocity of the transfusion pump 6 are expressed by v1 and v2, respectively, as shown in FIG. 12, the following absolute condition must be satisfied.

$$tN \cdot v2 > tR \cdot v1 \quad (24)$$

In practice, however, the predetermined amount of the mixed blood and transfusion solution, which is to be returned to the blood vessel, becomes considerably greater than the amount of the blood once drawn into the flow-through cell because the blood once drawn into the flow-through cell mixed with the transfusion solution, and, therefore, if it is excessively great, there may arise a problem in that the amount of transfusion solution to be drained into the drain container will become small with a corresponding increase in amount of the transfusion solution being transfused into the blood vessel. Accordingly, the length of time tN is preferred to satisfy the following relationship.

$$2.5tR \cdot v1 > tN \cdot v2 > 1.5tR \cdot v1$$

The reason that the valve device 77 is brought into the first state the predetermined time tM prior to the termination of the drive of the transfusion pump in the first direction (the start of drive of the transfusion pump in the first direction) is for the purpose of facilitating a smooth extraction of the blood into the flow-through cell simultaneously with the start of drive of the transfusion pump in the first direction. If this predetermined time tM is excessively small, for example, smaller than 1 second, the valve device 77 will remain in the second state even shortly after the start of drive of the transfusion pump in the second direction because of an error in time with the consequence that the transfusion solution once drained through the drain tube 72 will be possibly drawn again towards the flow-through cell 3. On the other hand, if the predetermined time tM is excessively great, the period in which the valve device 77 is in the second state during the drive of the transfusion pump 6 in the first direction will be shortened with the consequence that the amount of the transfusion solution to be drained will be reduced accompanied by the corresponding increase of the transfusion solution being transfused into the blood vessel. Therefore, the predetermined time tM is preferred to be within the range of 1 second to 20 seconds.

Table 3 below illustrates an example of operating conditions.

TABLE 3

| | CONDITION I | |
|---|---|---|
| Cycle Time tT | 10 minutes | |
| Solution Flow Velocity v2 | 350 μl/min. | |
| Reverse Flow Volume QR | 350 μl/min. | (= v1 · tR) |
| Partial Solu. Drain Time | 420 secs. (Time band:170-590 secs.) | 0* |
| Amt. of Solution Injected | 53 ml/day | 350 ml/day* |
| | CONDITION II | |
| Cycle Time tT | 5 minutes | |
| Solution Flow Velocity v2 | 390 μl/min. | |
| Reverse Flow Volume QR | 330 μl/min. | (= v1 · tR) |
| Partial Solu. Drain Time | 150 secs. (Time band:140-290 secs.) | 0* |
| Amt. of Solution Injected | 73 ml/day | 350 ml/day* |

[Note]
*indicates the case illustrated for the purpose of comparison, wherein the total amount of the transfusion solution is transfused into the blood vessel during each pumping cycle. It is to be noted that, in both of the Conditions I and II, the reverse flow velocity v1 is 330 μl/min, the reverse flow velocity v2 = v3, and the length of time tR during which the transfusion pump is driven in the second direction is 1 minute.

As can be understood from Table 3 above, according to the second preferred embodiment of the present invention wherein a portion of the transfusion solution is drained during each pumping cycle, the amount of the transfusion solution transfused into the blood vessel per day is reduced to about 1/7 (53/350) under Condition I and to about 1/5 (73/350) under Condition II. Moreover, if the amount of heparin added is assumed to be 3,000 units per 500 milliliter of transfusion solution, the amount of heparin transfused together with the transfusion solution can be reduced to about 320 units under Condition I and to about 440 units under Condition II as compared with 3,000 units of heparin transfused when the total amount of the transfusion solution is transfused. This should bring about a benefit on the part of the severely ill patients who have just received the surgical operation as well as the patients who are aspirated.

It is to be noted that, under any one of Conditions I and II, the blood once drawn from the blood vessel is not substantially drained into the drain container 73, and the result of measurement with the use of the apparatus according to the second preferred embodiment of the present invention parallels that with the use of the apparatus according to the previous embodiment.

Figure 13:
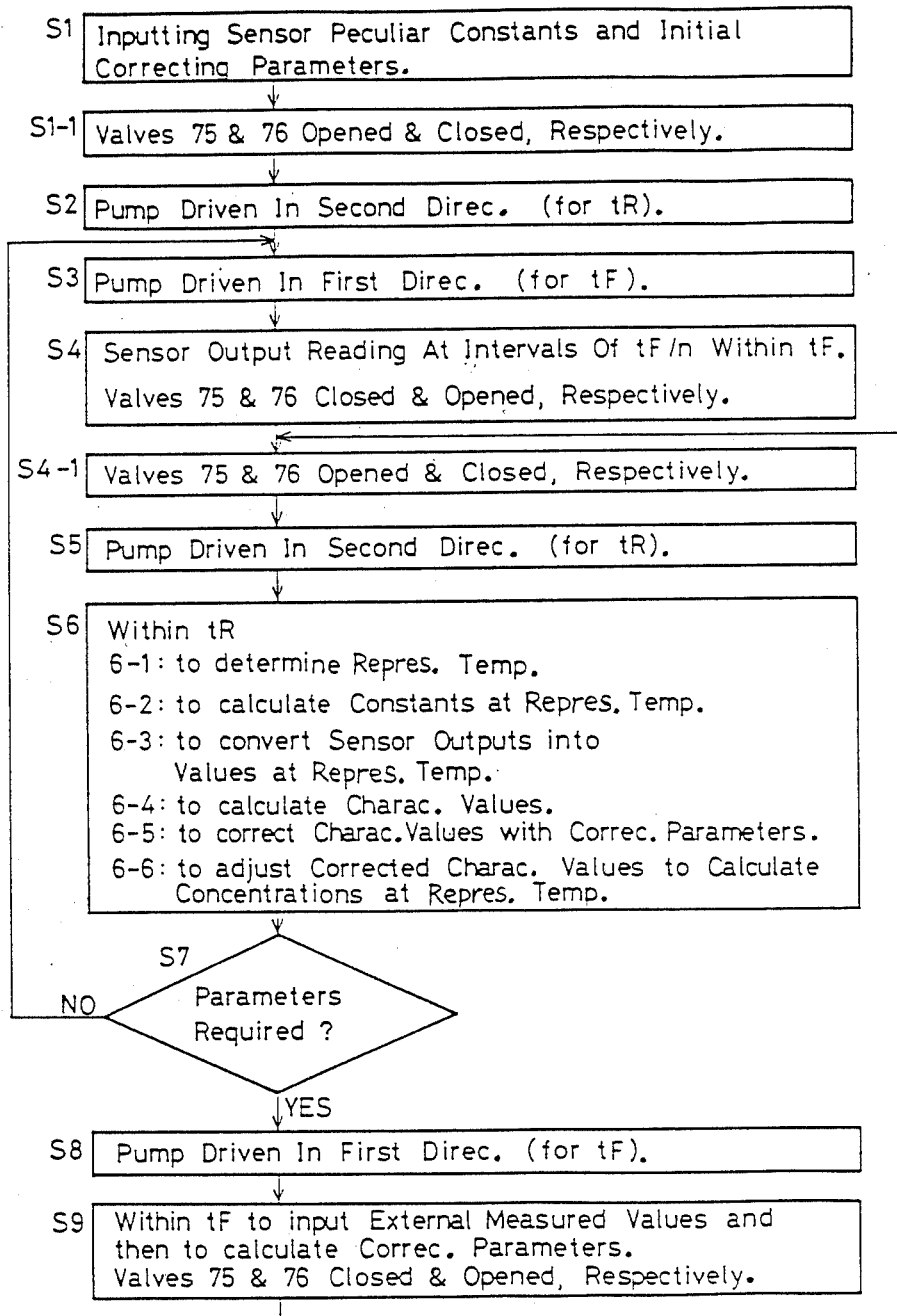
FIG. 13 is a flow chart showing the sequence of operation of a processing device used in the blood component monitoring apparatus of FIG. 10.

The operating program of the apparatus according to the second preferred embodiment is shown in FIG. 13 and is substantially similar to that shown in FIG. 6 in connection with the previous embodiment except that additional steps S1-1 and S4-1 are added between steps S1 and S2 and between steps S4 and S5 of the flow chart of FIG. 6 and that the contents of steps S4 and S9 of FIG. 6 are modified to include the operation of the valve device 77. Therefore, in describing the program of FIG. 13, only the differences relative to the program shown in FIG. 6 will now be described.

Referring to FIG. 13, at step S1-1, the valve device 77 is brought into the first state in which the blood and drain valves 75 and 76 are opened and closed, respectively, before the transfusion pump 6 is driven in the second direction at step S2.

After the predetermined time, that is, the time tN subsequent to the start of drive of the transfusion pump 6 in the first direction, and after the valve device 77 has been switched to assume the second state in which the blood and drain valves 75 and 76 are closed and opened, respectively, at step S4, to initiate the drainage of the transfusion solution, the valve assembly 77 is caused, at step S4-1, to assume the first state at the timing of time tM prior to the start of drive of the transfusion pump 6 in the second direction to open and close the blood and drain valves 75 and 76, respectively, followed by step S5 at which the transfusion pump 6 is driven in the second direction. Also, as is the case with step S4, the valve device 77 is switched to assume the second state, wherein the blood and drain valves 75 and 76 are closed and opened, respectively, the predetermined time tN subsequent to the start of drive of the transfusion pump 6 in the first direction to initiate the drainage of the transfusion solution towards the drain container 73.

From the foregoing description of the present invention made in connection with the preferred embodiments thereof, it is possible to acquire the accurate result of measurement of the chemical properties of the blood substances of interest in which the temperature dependent change has been compensated for. It is believed that the present invention has for the first time rendered the blood component monitoring apparatus of transfusion type to a practically acceptable and reliable level. Moreover, since the necessity of use of the constant temperature bath for maintaining the temperature inside the flow-through cell at a predetermined value at all times has successfully been dispensed with, the overall size of the apparatus can be rendered compact and simple for use at a bedside.

Furthermore, because the adsorption of protein to the sensors has successfully been minimized, the monitoring and measurement of the chemical properties of the blood substances of interest can be performed substantially continuously for a prolonged period of time with no time-consuming and complicated handling procedures substantially required.

Although the present invention has been fully described in connection with the preferred embodiments thereof with reference to the accompanying drawings taken only for the illustrative purpose, those skilled in the art can, upon the reading of the disclosure made by the inventors of the present invention, readily conceive numerous changes and modifications within the framework of the concept of the present invention. By way of example, if desired, the functions (B) and (E) associated with the problems (1) and (3) may not be always necessary and, in such case, the flow regulating means 18 and the adjusting means 22, both shown in FIG. 1, may not be utilized.

Moreover, the functions (C) and (E) associated with the problems (2) and (3) may, depending on the situation, not be always necessary and, in such case, the representative temperature setting means 19 and the temperature compensating means 20, both shown in FIG. 1, may not be utilized as in the second preferred embodiment described hereinbefore.

Accordingly, such changes and modifications are to be understood as included within the scope of the present invention as defined by the appended claims unless they depart therefrom.

What is claimed is:

1. A blood component monitoring system for monitoring chemical substances of interest in blood, which comprises:

a transfusion circuit including a flow-through cell adapted to be fluid-connected with a blood vessel through an indwelling catheter, a reservoir for accommodating a quantity of physiologically compatible sensor correcting solution, a connecting tubing extending between the reservoir and the flow-through cell and a transfusion pump;

a detector unit including a temperature sensor and a chemical sensitive sensor device both incorporated inside the flow-through cell;

a transfusion pump drive circuit for controlling operation of the transfusion pump;

a sensor drive circuit for driving the temperature sensor and the chemical sensitive sensor device;

a processing unit for controlling both of the transfusion pump drive circuit and the sensor drive circuit and for reading respective outputs from the temperature sensor and the chemical sensitive sensor device and converting the outputs into respective measured values; and an output device for externally outputting the measured values;

said processing unit including pump control means for controlling the pump drive circuit to drive the transfusion pump alternately in first and second directions opposite to each other according to a predetermined operating program, said first direction being such that physiologically compatible transfusion solution is introduced from the flow-through cell towards the blood vessel, said second direction being such that blood is drawn from the blood vessel towards the flow-through cell, representative temperature setting means for setting as a representative temperature the temperature of the detector unit which is detected by the temperature sensor at a particular timing during each pumping cycle of the transfusion pump when the transfusion pump has been driven according to the predetermined operating program, temperature compensating means for converting the output from the chemical sensitive sensor device into an output corresponding to the representative temperature according to a predetermined temperature compensating equation on the basis of the output from the chemical sensitive sensor device and the output from the temperature sensor both read out during each pumping cycle while the transfusion pump is being driven according to the predetermined operating program, and correcting means for correcting a characteristic value, based on the amplitude of the converted output, according to a predetermined correction equation to calculate the concentration of one or more chemical substances in the blood and then to apply a signal indicative of the calculated concentration to the output device.

2. The monitoring system as claimed in claim 1, wherein the processing unit further includes a flow regulator operable to control for the flow to establish the following relationship;

$$4.0 \leq QF/QR \leq 30$$

wherein QF represents the volume of flow of the physiologically compatible transfusion solution during the drive of the transfusion pump in the first direction, and QR represents the volume of flow of the physiologically compatible transfusion solution during the drive of the transfusion pump in the second direction.

3. The monitoring system as claimed in claim 1, wherein the processing unit further includes adjusting means for adjusting the measured values of the chemical substances fed from the correcting means so that the measured values of the chemical substances in the blood which are given by the blood component monitoring system can match with the measured values of the same substances in the same blood which are given by a different and separate monitoring system, said adjusting means being also operable to output the adjusted measured values to the output device.

4. The monitoring system as claimed in claim 3, wherein the adjusting means adjusts the measured values of the chemical substances, fed from the correcting means, according to predetermined correcting parameters which are empirically or experimentally determined with the use of the monitoring system and the different and separate monitoring system.

5. The monitoring system as claimed in claim 3, wherein the adjusting means is operable to calculate correcting parameters by comparing the respective measured values obtained with the use of the monitoring system and the different and separate monitoring system both being operated simultaneously with each other, and also to adjust the measured values from the correcting means with the use of the calculated parameters so determined.

6. The monitoring apparatus as claimed in claim 1, further comprising a drain tubing branched off from a portion of the indwelling catheter between the flow-through cell and the blood vessel, a valve device for selectively closing and opening the indwelling catheter and selectively closing and opening the drain tubing in a manner opposite to the closing and opening of the indwelling catheter, and a valve drive circuit for controlling the valve device, and wherein said processing unit further includes valve control means for controlling the valve drive circuit according to a predetermined program to actuate the valve device to cause the indwelling catheter and the drain tubing to open and close, respectively, during a period in which the volume of blood and transfusion solution moving during the drive of the transfusion pump in the first direction attains a predetermined value subsequent to the start of drive of the transfusion pump in the first direction and also to close and open the indwelling catheter and the drain tubing, respectively, when the volume exceeds the predetermined value, said predetermined volume being selected to be greater than the volume of blood and transfusion solution moving during the drive of the transfusion pump in the second direction.

7. The monitoring system as claimed in claim 6, wherein the predetermined volume is of a value within the range of 1.5 to 2.5 times the volume of blood and transfusion solution moving during the drive of the transfusion pump in the second direction.

8. A blood component monitoring system for monitoring chemical substances of interest in blood, which comprises:

a transfusion circuit including a flow-through cell adapted to be fluid-connected with a blood vessel through an indwelling catheter, a reservoir for accommodating a quantity of physiologically compatible sensor correcting solution, a connecting tubing extending between the reservoir and the flow-through cell and a transfusion pump;

a detector unit including a temperature sensor and a chemical sensitive sensor device both incorporated inside the flow-through cell;

a transfusion pump drive circuit for controlling operation of the transfusion pump;

a sensor drive circuit for driving the temperature sensor and the chemical sensitive sensor device;

a processing unit for controlling both of the transfusion pump drive circuit and the sensor drive circuit and for reading respective outputs from the temperature sensor and the chemical sensitive sensor device and converting the outputs into respective measured values; and an output device for externally outputting the measured values;

said processing unit including
pump control means for controlling the transfusion pump drive circuit to drive the transfusion pump alternately in first and second directions opposite to each other according to a predetermined operating program, said first direction being such that physiologically compatible transfusion solution is introduced from the flow-through cell towards the blood vessel, said second direction being such that blood is drawn from the blood vessel towards the flow-through cell, flow regulating means operable to control the flow to establish the following relationship:

$$4.0 \leq QF/QR \leq 30$$

wherein QF represents the volume of flow of the physiologically compatible transfusion solution during the drive of the transfusion pump in the first direction, and QR represents the volume of flow of the physiologically compatible transfusion solution during the drive of the transfusion pump in the second direction and correcting means for correcting a characteristic value, based on the amplitude of the converted output, according to a predetermined correction equation to calculate the concentration of one or more chemical substances in the blood and then to apply a signal indicative of the calculated concentration to the output device.

9. The monitoring system as claimed in claim 8, further comprising a drain tubing branched off from a portion of the indwelling catheter between the flow-through cell and the blood vessel, a valve device for selectively closing and opening the indwelling catheter and selectively closing and opening the drain tubing in a manner opposite to the closing and opening of the indwelling catheter, and a valve drive circuit for controlling the valve device, and wherein said processing unit further includes valve control means for controlling the valve drive circuit according to a predetermined program to actuate the the valve device to cause the indwelling catheter and the drain tubing to open and close, respectively, during a period in which said first mentioned volume attains a predetermined value subsequent to the start of drive of the transfusion pump in the first direction and also to close and open the indwelling catheter and the drain tubing, respectively, when said first mentioned volume QF exceeds the predetermined value, said predetermined volume being selected to be greater than said second mentioned volume QR.

10. The monitoring system as claimed in claim 9, wherein said predetermined volume is of a value within the range of 1.5 to 2.5 times the second mentioned volume QR.

* * * * *